(12) United States Patent
Lubon et al.

(10) Patent No.: US 6,262,336 B1
(45) Date of Patent: *Jul. 17, 2001

(54) EXPRESSION OF A HETEROLOGOUS PROTEIN C IN MAMMARY TISSUE OF TRANSGENIC ANIMALS USING A LONG WHEY ACIDIC PROTEIN PROMOTER

(75) Inventors: Henryk Lubon, Derwood, MD (US); William N. Drohan, Springfield, VA (US); Lothar Hennighausen, Chevy Chase, MD (US); William H. Velander, Blacksburg, VA (US)

(73) Assignees: American Red Cross, Rockville, MD (US); Virginia Tech Intellectual Properties, Inc., Blacksburg, VA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/321,831

(22) Filed: May 28, 1999

Related U.S. Application Data

(63) Continuation-in-part of application No. 09/184,063, filed on Nov. 2, 1998, now abandoned, and a continuation-in-part of application No. PCT/US98/02638, filed on Feb. 13, 1998, and a continuation-in-part of application No. 08/443,184, filed on May 17, 1995, which is a continuation-in-part of application No. 08/198,068, filed on Feb. 18, 1994, now abandoned, which is a continuation of application No. 07/943,246, filed on Sep. 10, 1992, now Pat. No. 5,831,141, which is a continuation-in-part of application No. 07/638,995, filed on Jan. 11, 1991, now abandoned.

(51) Int. Cl.[7] .................. A01K 67/027; C12P 21/00; C07H 21/04
(52) U.S. Cl. ................. 800/14; 800/15; 800/16; 800/17; 800/18; 800/7; 536/24.1
(58) Field of Search .................. 800/7, 14, 15, 800/16, 17, 18; 536/23.1, 24.1; 435/320.1

(56) References Cited

U.S. PATENT DOCUMENTS

| | | |
|---|---|---|
| 4,775,624 | 10/1988 | Bang et al. . |
| 4,775,642 | 10/1988 | Bang . |
| 4,873,316 | 10/1989 | Meade et al. . |
| 4,959,318 | 9/1990 | Foster . |
| 4,968,626 | 11/1990 | Foster . |
| 4,992,373 | 2/1991 | Bang et al. . |
| 5,831,141 | * 11/1998 | Lubon et al. ............ 800/2 |

FOREIGN PATENT DOCUMENTS

| | | |
|---|---|---|
| 0 264 166 | 4/1988 | (EP) . |
| 0 279 582 | 8/1988 | (EP) . |
| 88/00239 | 1/1988 | (WO) . |
| 88/01648 | 3/1988 | (WO) . |
| 90/05188 | 5/1990 | (WO) . |
| 91/08216 | 6/1991 | (WO) . |
| 92/11358 | 7/1992 | (WO) . |

OTHER PUBLICATIONS

Denman et al.; "Transgenic Expression of a Variant of Human tPA in Goat Milk: Purification and Characterization of the Recombinant Enzyme"; Bio/Technology; vol. 9; Sep. 1991; pp. 839–843.

Ebert et al.; "Transgenic Production of a Variant of Human tPA in Goat Milk: Generation of Transgenic Goats and Analysis of Expression" Bio/Technology; vol. 9; Sep. 1991; pp. 835–838.

Gordon et al.; "Production of Human Tissue Plasminogen Activation in Transgenic Mouse Milk"; Bio/Technology; vol. 5; Nov. 1987; pp. 1183–1187.

Krimpenfort et al.; "Generation of Transgenic Dairy Cattle Using 'In Vitro' Embryo Production"; Bio/Technology; vol. 9; Sep. 1991; pp. 844–847.

Walls et al.; "Amplification of Multicistronic Plasmids in the Human 293 Cell Line and Secretion of Correctly Processed Recombinant Human Protein C"; Gene; vol. 81, 1989; pp. 139–149.

Wright et al.; "High Level Expression of Active Human Alpha–1–Antitrypsin in the Milk of Transgenic Sheep"; Bio/Technology; vol. 9; Sep. 1991; p. 830.

Yan et al.; "Characterization and Novel Purification of Recombinant Human Protein C. from Three Mammalian Cell Lines"; Bio/Technology; vol. 8, Jul. 1990; pp. 665–661.

Velander et al.; "The Expression of Human Protein C in the Milk of Transgenic of the Mice"; Abstract Presented at the 1990 Annual Meeting; (Nov. 11–16, 1999); American Institute of Chemical Engineering.

Grinnell et al.; "Native and Modified Recombinant Human Protein C and related Anticoagulants"; Chapter 3, Bruley and Drohan, Eds; 1990.

Wydro; "Transgenic Production of Protein C" in "Protein C and Related Anticoagulants"; an International Symposium; Held in Feb. 26–27, 1992 in San Diego, CA.

Hogan et al.; "Manipulating the Mouse Embryo"; Cold Spring Harbor Laboratory; 1981; pp. 155–203.

(List continued on next page.)

*Primary Examiner*—Deborah Crouch
(74) *Attorney, Agent, or Firm*—Foley & Lardner

(57) ABSTRACT

An isolated DNA sequence which regulates the expression of a heterologous gene composed of a mouse whey acidic protein promoter having a length of greater than about 2.4 kb extending upstream from the unique KpnI site in the mouse whey acidic protein gene is disclosed. Specifically a mouse whey acidic protein promoter of about 4.1–4.2 kb in length extending upstream from the unique KpnI site is preferred. This mouse whey acid protein promoter is operably linked to a DNA sequence encoding a heterologous polypeptide and used to prepare transgenic non-human mammals expressing the heterologous polypeptide in their milk. Particularly efficient expression of both cDNAs and genomic DNAs encoding heterologous polypeptides was obtained in transgenic non-human mammals using this promoter, known as the long whey acidic protein promoter.

29 Claims, 23 Drawing Sheets

OTHER PUBLICATIONS

Grinnell et al.; "Trans–activated Expression of Fully Gamma–carboxylated Recombinant Human Protein C, An Antithrombotic Factor"; Biotechnology; vol. 5; pp. 1189–1192.

Pittius et al.; "A Milk Protein Gene Promoter Directs the Expression of Human Tissue Plasminogen Activator cDNA to the Mammary Gland in Transgenic Mice"; Proc. Natl. Acad. Sci., U.S.A.; vol. 85; pp. 5874–5878.

Colpan et al.; "HPLC of High–molecular–weight Nucleic Acids on the Macroporous Ion Exchange, Nucleogen"; J. Chromatography; vol. 296;; 1984; pp. 339–353.

Clark et al.; "Pharmaceuticals From Transgenic Livestock"; Tibtech; vol. 5; 1987; pp. 20–24.

Campbell et al.; "Comparison of the Whey Acid Protein Genes of the Rat and Mouse"; Nucleic Acids Research; vol. 12; 1984; pp. 8686–8697.

Bondioli et al.; Transgenic Animals; Proceeding of the Sympostium on Transgenic; Technology, ed.; pp. 265–273.

Hill et al.; Theriogenology 37; 1992; p. 222.

Masseyl; J. Reprod. Fert. Suppl. 41; 1990; pp. 199–288.

Biery et al.; Theriogenology 29; 1988; p. 224.

Genetic Engeneering News; Oct. 15, 1995; pp. 8–9.

Palmito et al.; Ann. Reo. Genet 20; 1986, pp. 465–499.

Velander et al.; Procec. Natl. Acad. Sci. 89; 1992; pp. 12003–12007.

Plutzky et al., Procec. Natl. Acad. Sci. 83; 1986; pp. 546–550.

Young et al.; "Expression of Human Protein C in the Milk of Transgenic Mice"; J. Cell Biochem. Suppl.; vol. 15A; No. 174; 1991; Abstract No. B 025.

Bischoff et al.; "A 17.6 KBP region Located Upstream of the Rabbit Wap Gene Directs High Level Expression of a Functional Human Protein Variant in Transgenic Mouse Milk, Febs"; vol. 305, No. 3; Jul. 1992; pp. 265–268.

Hennighousin; Protein Expression and Purifucastion: vol. 1; 1990; pp. 3–8.

Brinster et al.; Proced. Natl. Acad. Sci. 88; 1988; pp. 836–840.

Choo et al (1987) Nucleic Acids Res. 15, 871–894.*

Foster et al (1985) PNAS 82, 4673–4677.*

* cited by examiner

WAP-ProC Primer Pairs

| Primer Pairs | Fragment Length |
|---|---|
| a - c | 441 |
| b - c | 324 |
| b - d | 563 |
| a - e (endogenous) | 222 |

Other Primer Pairs

| | |
|---|---|
| 18S rRNA | 337 |
| Mouse LDH | 331 |
| Pig UPA | 319 |

FIG. 9A

```
   1 gatctctcca tctaaggacc agccatgagc cattgagcag ccacagaaaa catttactat
  61 ttatttatct atttattata tttaaataaa cataaaatat aaacatatca atgttgttaa
 121 tgttttattc atgtgtattt gttaatattt atatttatt aatatttatt aagacttgtc
 181 tctgtgtgtg tgtgtgtgca tgtgtgtgtg catgtgtgag caggtagttg gtatacaggt
 241 gcataaagag agcgagagct ttgttctaga gttggaacta caggtagttg tgaggcaaca
 301 gatttgaatc ctggagacaa acttggtcct ctacaagatc accaagtaat ctttacaact
 361 gagccatctt tccaggccct gaagataatt tttaatggaa taggggact aataattttt
 421 caaagattt atttatttgc atttattcgg ttctgaatat tttacctgca tgtaagtgcc
 481 acaaaagact agaaggagga ggcaggtcct agaactggac ctaggccat cctcggctac
 541 tatntgggct ctgggaatca agcctgcatc ttcagcaaga gcaacaagtg ctcttaacct
 601 gttgaccat gtgtgtttat gtatcaagca cagtgagctg ctttctgtaga gggtgccaa
 661 ggcctgaaca ttctcagcag actggaacac tcctctcaga cccaaggttg cttctactga gggaaaactc
 721 agggactcct cccaggcctc aagaggtaga gagtggtaga cccaaggttg gtgggcccct tttccaaggt gggatcaac
 781 tgtgcctaag gagtggtaga gacccctact gtccttcaag atccacaaac ctgcgagctt gtccaagtc
 841 ttgatgctct gacccctact gtccttcaag actgaaaaaa atcccctag actgtaaagg gtttcctggg
 901 tacctctaaa tcacagcatg actgaaaaaa atcccctag actgtaaagg gtttcctggg
 961 cctgttaga aaccactct ctatcacctg ctaattctcc acagtccctg ttccaatgga
1021 gaccctcctg gcaggtttct gaaggaggga gtagcaggtc aaacttctcc tctcatcaga
1081 ggagaggcca ggccctcctc cttctcacca aagggctca acacctcacc ccttctcagc
1141 acttctgcct tctcacttaa acatggtgac ccagactct gtgccaacaa tcactccctc
1201 ctgggcac ctctggaggc tgcaccccgt cgctggacc caacacagat gggctagcta
1261 acgagccaca agggaacatg ccagagcac atagtgcagt agagcagcca tgcagctcgt
1321 acctccttgc tgttgcttag agcagccggt gccagctggg gtgtctaaca caattaccct
1381 tggtgctgct gagcagggga caggccaagg agctttggggg aaggagacac actgtatacg
```

FIG. 9B

```
1441 gatatgactg aggcatatga ggggtgtagg agagcctcag aatgagcagc agagcctatg
1501 actaaggtct gacatagcac agtgacaagg atgacatgta gtcgtgactt cactgaagag
1561 ggagagactc tcactcagaa ttcctaagca ccatggccaa gaatggggca agctgttcat
1621 ccaggagcca taaagcacta caagaaagaa gcaagctcgt gggcaggca gcctgtcctc
1681 ctccatcacc ctgtcctcct cttccaccct gtccactgct caggttttta gggaaaattc
1741 cagcacagct gacccatag gacaaaaagt gcagtgtgtg tactaccaaa accctgggtg
1801 tcctttttcc accctagccg agcagagttg atggggcagg aaagagccta gcatactgga
1861 agcacacagg ctcaagactg gcaggccaaa gaaccagaac acccagggc ataagaaccc
1921 catgccctt gcgcctgggc ctggtgaatt cagagtaatg tcttcattcc tagaaccttc
1981 tggcttccg acctggcctg caggctctga gagatgtgtg cacctcatga actccttgtt
2041 cagccaggc ctctctgtcc tcctacact tccccaccac acaggaacac atgtcctcaa
2101 ctgaccagtg tcaccctggg cctcaaggct aggttccctt gagtactggg aacacagaa
2161 tagacttctg ctctccccct tgtccacaca gagtgcagag agcaagggtt ctggttcatg
2221 tccacagtt gccccctaaa accgatgtga tatagcctc actggcctag agctcactac
2281 ataaacaggc tggcctgaac ccacagatct gtctgccttt gactcctact gctgggatca
2341 aaggtgtgag ccaccatgca acgctctgaa actgattctt tagaagctaa gaaaatgctt
2401 caaaatggca gtagccttgg cgtggagatg ggttagtggt taagagaact gactgctctt
2461 ccagagagag agagagagag agagagagag agagagagag agagagagag agctggaaga
2521 gggagatctg ggaagtctgc tggctttata tgctgaccat atatagtcac ctgtgtttac
2581 aactgttgct catcactttg aaatctcagt ggtttcctcc tttgagcctg tgtctgtaag
2641 ttacacagga cagtggtact ataggcaaga ataacagcca gtgggcatag gacacagagt
2701 gcatgggccc cagcaagatg cagagagaac agagaagaac agagcttctgg ctcctaagac acaggcctt
```

FIG. 9C

```
2761  ctggaaact  caagcagcca  agcaaccta  gccagccct  tcctgtggc  cctccttctg
2821  ttccagcaaa  ggcggaaatg  ggaacagggg  tggaagcaga  gcattggcag  agcatagtta
2881  tgacttagtc  ttgactaaca  caagcatggc  agtagcctga  cagtggccta  aatgtggga
2941  tgactgcttt  agatgaggat  gacttgccta  gatgggatg   actgccttag  atggggatga
3001  ctgccttaga  tggggatgac  tgccttagat  ggaacaacaa  acatctatgg  gcatgctgtg
3061  gaacactggc  ccacacacag  aactgaagca  ctggcaattt  ccacagggca  gttaaaccta
3121  aaagcatgct  cacactcaac  aggctgccgg  aactcatgag  acacctggaa  tagacgaatg
3181  tagaaacaga  gcagagagtt  ggttgccaag  gtctggggc   tcagaggaca  agcaagaggc
3241  gcggctttcc  tttggggctg  gcatgaaagg  aaatatcgag  gttacagcct  gagagggctt
3301  ccctgacac   ttcgtattca  aagaggccat  gggcaccagt  gaagacaaag  gagtatgcc
3361  tgcaccacag  gctggcnctg  acagtcagta  agcacacagt  cactctgggt  catcccatcc
3421  ccttccttgc  aagagaaatc  aaggaaatgt  cccgagaaca  atgggcaca   gtgccagcag
3481  gacatctctt  cctgcccaat  gacacccttg  gcacagtatg  ggcctttctg  ggaagttggc
3541  cttccaatgt  gctctgcaca  ggcagctcct  tttcaatgta  tgcccgacac  tctctacatg
3601  gagcaagcgc  ctccacactc  ttagaagaat  ttttagaaaa  ctccagaaaa  gcaccaggag
3661  aagtcaccct  cagatgtagc  ccggactcga  gcctttgctca  aaacctcctg  tcttgttttc
3721  tatgtgactg  tacaaatttg  gagctcagaa  ttgcctttgt  ctgtgatggg  ttccaaccca
3781  accactcaaa  gtgacacttg  tcacatttgt  cactgatcct  attctttctt  ttttctgctcc
3841  ttcatttct   ccgctttcat  aataaacaag  tattacttt   taagtgggg   aaaaatgac
3901  caccctaca   aggacttttt  taaaaatggc  ctccattgtg  gcccttgttc  ctggcagcct
3961  gggcctgctc  tctctgtgtg  gccaagaagg  aagtgttgta  gcccatctag  agctgtgcca
4021  gcctcttccc  ccaccccacc  cccaaagtct  tccttcctgtg  ggtcctttaa  atgcatccca
4081  gacactcaga  cagccatcag  tcacttgcct  gacaccggta  cc
```

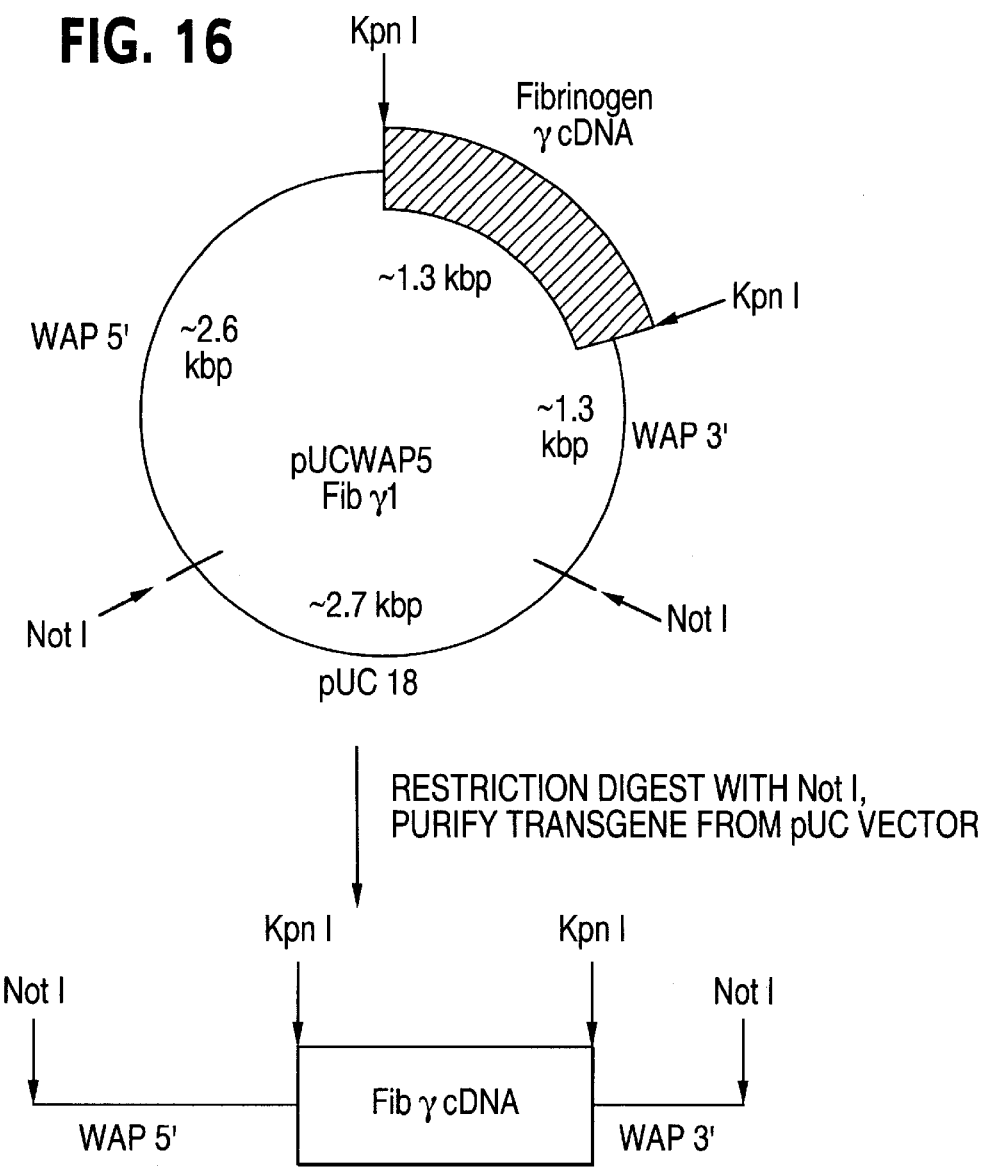

SEQUENCE LISTING

<160> NUMBER OF SEQ ID NOS: 12

<210> SEQ ID NO 1
<211> LENGTH: 4122
<212> TYPE: DNA
<213> ORGANISM: WAP gene promoter fragment from the C57B/6 mouse strain
<220> FEATURE:
<221> NAME/KEY: misc_feature
<222> LOCATION: (544)..(544)
<223> OTHER INFORMATION: "n" is unknown
<221> NAME/KEY: misc_feature
<222> LOCATION: (3377)..(544)
<223> OTHER INFORMATION: "n" is unknown

<400> SEQUENCE: 1

-continued

```
gatctctcca tctaaggacc agccatgagc cattgagcag ccacagaaaa catttactat      60
ttatttatct atttattata tttaaataaa cataaaatat aaacatatca atgttgttaa     120
tgttttattc atgtgtattt gttaatattt ataacttact aatatttatt aagacttgtc     180
tctgtgtgtg tgtgtgtgca tgtgtgtgtg catgtgtgag gtatacatgt gtatacaggt     240
gcataaagag agcgagagct tgttctaga gttggaacta caggtagttg tgaggcaaca      300
gatttgaatc ctggagacaa acttggtcct ctacaagatc accaagtaat ctttacaact     360
gagccatctt tccaggccct gaagataatt tttaatggaa tagggggact aataattttt     420
caaagatttt atttatttgc attttatcgg ttctgaatat tttacctgca tgtaagtgcc     480
acaaaagact agaaggagga ggcaggtcct agaactggac ctagggccat cctcggctac     540
tatntgggct ctgggaatct agcctgcatc ttcagcaaga gcaacaagtg ctcttaacct     600
gttgacccat gtgtgtttat gtatcaagca cagtgagctg cttctgtaga gggtggccaa     660
ggcctgaaca ttctcagcag actggaacac ctaacccaat ctctacttga gggaaaactc     720
agggactcct cccaggcatc tcctctcaga cccaaggttg agcccaggag ctccttgccc     780
tgtgcctaag gagtggtaga agaggaagt gtgggcccct tttccaaggt ggggatcaac      840
ttgatgctct gaccctact gtccttcaag atccacaaac actgtaaagg gtttcctggg      900
tacctctaaa tcacagcatg actgaaaaaa atcccctag actgtaaagg gtttcctggg      960
cctgtttaga aaccacttct ctatcacctg ctaattctcc acagtccctg ttccaatgga    1020
gaccctcctg gcaggtttct gaaggaggga gtagcaggtc aaacttctcc tctcatcaga    1080
ggagaggcca ggccctcctc cttctcacca aagggctca acacctcacc ccttctcagc     1140
acttctgcct tctcacttaa acatggtgac cccagactct gtgccaacaa tcactccctc    1200
ctgggggcac ctctggaggc tgcaccccgt ccgctggacc caacacagat gggctagcta    1260
acgagccaca agggaacatg ccagagccac atagtgcagt agagcagcca tgcagctcgt    1320
acctccttgc tgttgcttag agcagccggt gccagctggg gtgtctaaca caattaccct    1380
tggtgctgct gagcagggga caggccaagg agctttgggg aaggagacac actgtatacg    1440
gatatgactg aggcatatga ggggtgtagg agagcctcag aatgagcagc aaggcctatg    1500
actaaggtct gacatagcac agtgacaagg atgacatgta gtcgtgactt cactgaagag    1560
ggagagactc tcactcagaa ttcctaagca ccatggccaa gaatggggca agctgttcat    1620
ccaggagcca taaagcacta caagaaagaa gcaagctcgt ggggcaggca gcctgtcctc    1680
ctccatcacc ctgtcctcct cttccaccct gtccactgct caggttttta gggaaaattc    1740
cagcacagct gaccccatag acaaaaagt gcagtgtgtg tactaccaaa accctgggtg     1800
tcctttttccc accctagccg agcagagttg atggggcagg aaagagccta gcatactgga   1860
agcacacagg ctcaagactg gcaggccaaa gaaccagaac accccagggc ataagaaccc    1920
catgccccctt gccgctgggc ctggtgaatt cagagtaatg tcttcattcc tagaaccttc   1980
tggcttcccg acctggcctg caggctctga gagatgtgtg cacctcatga actccttgtt    2040
cagccagggc ctctctgtcc tccctacact tccccaccac acaggaacac atgtcctcaa    2100
ctgaccagtg tcaccctggg cctcaaggct aggttccctt gagtactggg aacacaagaa    2160
tagacttctg ctctcccctc tgtccacaca gagtgcagag agcaagggtt ctggttcatg    2220
tcccacagtt gccccctaaa accgatgtga tatagccctc actggcctag agctcactac    2280
ataaacaggc tggcctgaac ccacagatct gtctgccttt gactcctact gctgggatca    2340
aaggtgtgag ccaccatgca acgctctgaa actgattctt tagaagctaa gaaaatgctt    2400
```

-continued

```
caaaatggca gtagccttgg cgtggagatg ggttagtggt taagagaact gactgctctt    2460
ccagagagag agagagagag agagagagag agagagagag agagagagag agctggaaga    2520
gggagatctg ggaagtctgc tggctttata tgctgaccat atatagtcac ctgtgtttac    2580
aactgttgct catcactttg aaatctcagt ggtttcctcc tttgagcctg tgtctgtaag    2640
ttacacagga cagtggtact ataggcaaga ataacagcca gtgggcatag gacacagagt    2700
gcatgggccc cagcaagatg cagagagaac agagctctgg ctcctaagac acagggcctt    2760
ctgggaaact caagcagcca agcaaccctg gccagccctt tcctggtggc cctccttctg    2820
ttccagcaaa ggcggaaatg ggaacagggg tggaagcaga gcattggcag agcataggta    2880
tgacttagtc ttgactaaca caagcatggc agtagcctga cagtggccta aatgtgggga    2940
tgactgcctt agatgaggat gactgcctta gatggggatg actgccttag atggggatga    3000
ctgccttaga tggggatgac tgccttagat ggaacaacaa acatctatgg gcatgctgtg    3060
gaacactggc ccacacacgg aactgaagca ctggcaattt ccacagggca gttaaaccta    3120
aaagcatgct cacactcaac aggctgccgg aactcatgag acacctggaa tagacgaatg    3180
tagaaacaga gcagagagtt ggttgccaag gtctgggggc tcagaggaca agcaagaggc    3240 gcggcttttcc tttggggctg gcatgaaagg aaatatcgag gttacagcct gagagggctt    3300
cccctgacac ttcgtattca aagaggccat gggcaccagt gaagacaaag gagtatggcc    3360
tgcaccacag gctggcnctg acagtcagta agcacacagt cactctgggt catcccatcc    3420
ccttccttgc aagagaaatc aaggaaatgt cccgagaaca atggggcaca gtgccagcag    3480
gacatctctt cctgcccaat gacacccttg gcacagtatg ggcccttctg ggaagttggc    3540
cttccaatgt gctctgcaca ggcagctcct tttcaatgta tgcccgacac tctctacatg    3600
gagcaagcgc ctccacactc ttagaagaat ttttagaaaa ctccagaaaa gcaccaggag    3660
aagtcaccct cagatgtagc ccggactcga gccttgctca aaacctcctg tcttgttttc    3720
tatgtgactg tacaaatttg gagctcagaa ttgcctttgt ctgtgatggg ttccaaccca    3780
accactcaaa gtgacacttg tcacatttgt cactgatcct atttcttctt tttctgctcc    3840 ttcatttttct ccgctttcat aataaacaag tattactttt taagtggggg aaaaaatgac    3900 caccccttaca aaggacttttt taaaaatggc ctccattgtg gcccttgttc ctggcagcct    3960
gggcctgctc tctctgtgtg gccaagaagg aagtgttgta gcccatctag agctgtgcca    4020
gcctcttccc ccaccccacc cccaaagtct tcctcctgtg ggtcctttaa atgcatccca    4080
gacactcaga cagccatcag tcacttgcct gacaccggta cc                       4122
```

<210> SEQ ID NO 2
<211> LENGTH: 20
<212> TYPE: DNA
<213> ORGANISM: primer

<400> SEQUENCE: 2

```
gctaggtacc atgcagcgcg                                                    20
```

<210> SEQ ID NO 3
<211> LENGTH: 21
<212> TYPE: DNA
<213> ORGANISM: primer

<400> SEQUENCE: 3

```
gtcaggtacc ttaagtgagc t                                                  21
```

```
<210> SEQ ID NO 4
<211> LENGTH: 21
<212> TYPE: DNA
<213> ORGANISM: primer

<400> SEQUENCE: 4
ggataacatc actcaaagca c                                              21

<210> SEQ ID NO 5
<211> LENGTH: 24
<212> TYPE: DNA
<213> ORGANISM: primer

<400> SEQUENCE: 5
tagcagcaga ttgaaagcat tatg                                           24

<210> SEQ ID NO 6
<211> LENGTH: 16
<212> TYPE: DNA
<213> ORGANISM: primer

<400> SEQUENCE: 6
gtgaactttg tagatc                                                    16

<210> SEQ ID NO 7
<211> LENGTH: 30
<212> TYPE: DNA
<213> ORGANISM: primer

<400> SEQUENCE: 7
gctaggtacc atgttttcca tgaggatcgt                                     30

<210> SEQ ID NO 8
<211> LENGTH: 30
<212> TYPE: DNA
<213> ORGANISM: primer

<400> SEQUENCE: 8
cagtggtacc ctagacaggg cgagatttag                                     30

<210> SEQ ID NO 9
<211> LENGTH: 30
<212> TYPE: DNA
<213> ORGANISM: primer

<400> SEQUENCE: 9
gctaggtacc atgaaaagaa tggtttcgtg                                     30

<210> SEQ ID NO 10
<211> LENGTH: 30
<212> TYPE: DNA
<213> ORGANISM: primer

<400> SEQUENCE: 10
cagtggtacc ctattgctgt gggaagaagg                                     30

<210> SEQ ID NO 11
<211> LENGTH: 30
<212> TYPE: DNA
<213> ORGANISM: primer

<400> SEQUENCE: 11
gctaggtacc atgagttggt ccttgcaccc                                     30
```

```
-continued

<210> SEQ ID NO 12
<211> LENGTH: 30
<212> TYPE: DNA
<213> ORGANISM: primer

<400> SEQUENCE: 12
cagtggtacc ttaaacgtct ccagcctgtt                                        30
```

EXPRESSION OF A HETEROLOGOUS PROTEIN C IN MAMMARY TISSUE OF TRANSGENIC ANIMALS USING A LONG WHEY ACIDIC PROTEIN PROMOTER

This application is a continuation-in-part of U.S. Ser. No. 09/184,063 filed on Nov. 2, 1998, which is a continuation of U.S. Ser. No. 07/943,246, filed Sep. 10, 1992, now U.S. Pat. No. 5,831,141, which is a continuation-in-part of U.S. Ser. No. 07/638,995, filed on Jan. 11, 1991, abandoned. This application is also a continuation-in-part of PCT/US98/02638 filed on Feb. 13, 1998, and a continuation-in-part of U.S. Ser. No. 08/443,184 filed on May 17, 1995, which is a continuation-in-part of U.S. Ser. No. 08/198,068 filed on Feb. 18, 1994, all of which are herein incorporated by reference in their entirety.

The present invention relates to an isolated DNA sequence which regulates the expression of a heterologous gene comprising a mouse whey acidic protein (WAP) promoter having a length of greater than about 2.4 kb extending upstream from the unique KpnI site in the mouse whey acidic protein. The present invention also relates to a transgenic non-human mammal containing a DNA sequence stably integrated in its genome, wherein the DNA sequence contains the mouse whey acidic protein promoter having a length of greater than about 2.4 kb extending upstream from the unique KpnI site in the mouse whey acidic protein gene and is operably linked to a DNA sequence encoding a heterologous polypeptide and a process of producing the heterologous polypeptide in the milk of the transgenic mammal. The DNA sequence can comprise cDNA or genomic DNA encoding the heterologous protein.

The present invention also relates to the production of natural and modified forms of the human coagulation factor protein C. In particular, the invention relates to a transgenic animal containing, stably incorporated in its genomic DNA, an exogenous gene which is expressed in tissue of the animal, specifically in mammary tissue, such that protein C is secreted into a body fluid of the animal, particularly into the milk produced by the animal. In particular, the invention relates to the production of natural and modified forms of protein C in the milk of a transgenic non-human mammal using a DNA molecule that comprises, a mouse whey acid protein promoter having a length of greater than about 2.4 kb extending upstream from the unique KpnI site in the mouse whey acidic protein gene, particularly the upper range of this length, which is herein referred to as the long whey acidic protein (WAP) promoter fragment and a cDNA or genomic DNA encoding human protein C. The long whey acidic protein promoter fragment also can be used to express high levels of other genes in cells, such as mammary cells of transgenic non-human mammals.

BACKGROUND OF THE INVENTION

Protein C is an important component of the coagulation system that has strong anticoagulant activity. In its active form it is a serine protease that proteolytically inactivates Factors Va and VIIIa.

Human protein C (hPC) is a 62 kD, disulfide-linked heterodimer consisting of a 25 kD light chain and a 41 kD heavy chain which circulates as an inactive zymogen in plasma. At the endothelial cell surface it is activated to activated protein C (APC) by limited thrombin proteolysis in the presence of thrombomodulin; cleavage of an Arg-Leu bond in the amino terminal portion of the heavy chain releases a 12 amino acid peptide. See generally Gardiner & Griffin in PROGRESS IN HEMATOLOGY, Vol. XIII at page 265–278 (Brown, Grune and Stratton, Inc. 1983).

Several regions of the molecule have important implications for function as an anticoagulant in the regulation of hemostasis. The amino terminal portion of the light chain contains the nine y-carboxyglutamic acid (Gla) residues required for calcium-dependent membrane binding and functional activation. Another post-translational modification is β-hydroxylation of aspartic acid reside 71, possibly required for calcium-dependent membrane binding which is independent of the binding activity of the Gla regions.

There are a variety of clinical situations for which protein C may prove beneficial. It may serve as replacement therapy in homozygous deficient infants suffering from purpura fulminans neonatalis. Other conditions include patients with a previous history of warfarin-induced skin necrosis who must have additional warfarin therapy, heparin-induced thrombocytopenia, septic shock for prevention of intravascular coagulation and organ damage, and for fibrinolytic therapy, as protein C can protect tPA from plasma inhibitor proteins. Table 1 represents one estimate of the number of individual cases of several clinical syndromes which might be treated by purified protein C. Because there has not been sufficient material available from plasma for clinical trials until recently, these data are necessarily based on an incomplete assessment of the therapeutic potential for protein C.

TABLE 1

PARTIAL ESTIMATE OF U.S. CLINICAL REQUIREMENTS FOR PROTEIN C AND ACTIVATED PROTEIN C

| Indication | Estimated Dose (mg) Per Treatment | # Treatments Per Year | Total U.S. Req. (Kg) |
| --- | --- | --- | --- |
| Septic Shock | 5–50 | 120,000 | 0.6–6.0 |
| Thrombolytic Therapy** | 10–100 | 800,000 | 8–80 |
| Hip Replacement | 10–100 | 200,000 | 2–20 |
| Homozygous Deficient | 3 | 100 × 365* | 0.10 |
| Heterozygous Deficient | 50 | 1,000 | 0.05 |
| Total | | | 10.8–106.2 |

*100 individuals in U.S. × 365 treatment/year
**Referes to the use of APC, following thrombolytic therapy, to prevent the reformation of blood clots.

The gene for human protein C has been cloned and sequenced, as has bovine protein C gene. See Forster et al., *Proc. Nat'l Acad. Sci. USA* 82: 4673 (1985); U.S. Pat. No. 4,775,624. It is synthesized as an inactive precursor that undergoes several proteolytic events during the processes of secretion and activation. First, a signal sequence as proteolytically removed upon secretion. A second proteolytic event removes the dipeptide lys156 arg157, producing the inactive zymogen, a two chain disulfide bridged protein, consisting of a light chain of 155 amino acids and a heavy chain of 262 amino acids. The zymogen is activated by a final proteolytic event that removes residues 158–169, yielding active protein C, a serine protease with potent anticoagulant activity. Beckmann et al., *Nucleic Acids Res.* 13: 5233 (1985).

In addition to proteolytic processing, human protein C undergoes several post-translation modifications. Perhaps most salient among these modifications is the γ-carboxylation of the first nine glutamic acid residues in protein C, by a vitamin K dependent enzyme. DiScipio & Davie, *Biochemistry* 18: 899 (1979). Gamma-carboxylation is required for anticoagulant activity, and is associated with $Ca^{2+}$-dependent membrane binding. The anticoagulant activity of protein C varies directly with the extent of γ-carboxylation, and the highest levels of activity are achieved only when γ-carboxylation of the sixth and seventh glutamic acid residues is effected. Zhang & Castellino, *Biochemistry* 29: 10829 (1990).

Protein C is also post-translationally modified by β-hydroxylation of aspartic acid 71. Drakenberg et al., *Proc. Nat'l Acad. Sci. USA* 80: 1802 (1983). Beta-hydroxylation may be important to protein C activity. Although its function is not known it has been suggested that it may be involved in γ-carboxyglutamic acid independent $Ca^{2+}$ binding, and it may be required for full anti-coagulant activity.

Human protein C is also glycosylated. Kisiel, *J. Clin. Invest.* 64: 761 (1979). It contains four potential N-linked glycosylation sites, located at Asn97, Asn248, Asn313 and Asn329. The first three signals match the consensus Asn-X-Ser/Thr glycosylation sequences, and are actively glycosylated. There is an atypical glycosylation signal at Asn329, Asn-X-Cys-Ser. The Asn329 signal is glycosylated in bovine protein C, but it is not yet known if Asn329 is glycosylated in human protein C. Miletich et al., *J. Biol. Chem.* 265: 11397 (1990). The pattern and extent of glycosylation can alter the physiological activity of protein C.

Until recently, human protein C for experimental and therapeutic use was obtained exclusively from human plasma. Unfortunately, the quantity of protein that can be obtained from human serum is limited. Furthermore, products derived from human serum pose difficulties of reliability, purity and safety.

The expression of therapeutic proteins by recombinant DNA technology is an attractive alternative to plasma production of protein C, in that it eliminates the risk of potential contamination with blood-borne viruses and theoretically provides an unlimited supply of product. But the complexity of the post-translational modifications, as discussed above, has rendered problematic the production of commercially useable amounts of suitably active protein C by expression in a heterologous host.

In fact, it has not been possible to produce vitamin K-dependent proteins like protein C at sufficiently high levels in an active form, despite efforts to do so using a variety of expression systems. See Grinnell et al. in Volume 11 of ADVANCES IN APPLIED BIOTECHNOLOGY SERIES, Chapter 3 (Gulf Publishing Co.). In particular, any prospect for expressing protein C in mammary glands of a transgenic animal and secreting the protein into milk, see, e.g., U.S. Pat. No. 4,873,316 (1989), is clouded by the fact that protein C is normally synthesized in the liver. Even HepG2 cell lines derived from human liver produce aberrant forms of protein C. Marlar & Fair (1985).

In this regard, it has been observed that a mouse mammary epithelial cell line (C-127) transfected with a bovine papilloma virus (BPV) vector bearing the cDNA for human protein C expressed protein C that was only 30–40% active. Further analysis revealed that the protein C contained diminished levels of γ-carboxyglutamic acid and little, if any, β-hydroxyaspartic acid. Suttie et al., *Thrombosis Res.* 44: 129 (1986). These experiments indicate that mouse mammary epithelial cells cannot perform all of the post-translational modifications necessary for obtaining suitably active protein C, which in turn casts doubt on the likelihood of obtaining such protein C from the milk of a transgenic mammal.

SUMMARY OF THE INVENTION

It is an object of the present invention to obtain and use an isolated DNA sequence which regulates the expression of a heterologous gene, wherein the DNA sequence comprises of a mouse whey acidic protein promoter having a length of greater than about 2.4 kb extending upstream from the unique KpnI site in the mouse whey acidic protein gene. The mouse whey acidic protein promoter of the present invention is more specifically an isolated DNA sequence comprising a mouse whey acidic protein promoter having a length of greater than about 2.4 kb to less than about 4.2 kb. The isolated DNA sequence may also encompass mouse whey acidic protein promoters that are functionally equivalent to the promoter activity of the mouse whey acidic 4.2 kb Sau3A-Kpn1 promoter.

It also is an object of the present invention to obtain and use an isolated DNA sequence comprising a mouse whey acidic protein promoter comprising at least the approximately mouse whey acidic protein 4.2 kb Sau3A-Kpn1 promoter.

It is a further object of the present invention to obtain and use an isolated DNA sequence comprising a mouse whey acidic protein promoter comprising the NotI-Kpn1 promoter of the mouse whey acidic protein gene.

It is an additional object of the present invention to operably link any of the disclosed mouse whey acidic protein promoters to a DNA sequence encoding a heterologous polypeptide and a 3'-untranslated region from a mammary gland-specific gene or a 3'-untranslated region active in a mammary gland. This 3'-untranslated region is preferably the 1.6 kb fragment of the mouse whey acidic protein gene. The DNA sequence encoding a heterologous polypeptide is intended to be any DNA sequence that is known and available to persons skilled in the art. The DNA sequence preferably encodes a blood protein or plasma protein, and more preferably encodes such blood proteins as protein C, Factor IX, fibrinogen, Factor VIII, thrombin, von Willebrand's factor, albumin, and α1-antitrypsin, as well as growth factors and antibodies.

It also is an object of the present invention to produce a transgenic non-human mammal containing a DNA sequence stably integrated in its genome, wherein the DNA sequence comprises a mouse whey acidic protein promoter having a length of greater than about 2.4 kb extending upstream from the unique KpnI site in the mouse whey acidic protein gene, operably linked to a DNA sequence encoding a heterologous polypeptide, whereby the polypeptide is expressed specifically in mammary cells of the transgenic mammal and the polypeptide comprises a signal peptide that is effective in directing the secretion of the polypeptide into the milk of said mammal.

In a highly preferred embodiment the promoter comprises substantially the 5' 4.2 kb Sau3A-Kpn1 promoter fragment of the mouse whey acidic protein gene, or a variant thereof. This 4.2 kb Sau3A-KpnI promoter may be contained in a longer DNA sequence to include polylinkers that will facilitate the construction of expression vectors, such as for example, introducing a NotI cloning site upstream from the Sau3A site.

In another aspect in a preferred embodiment the DNA sequence encoding a polypeptide having human protein C activity comprises portions of the non-coding regions of the human protein C gene. In a particularly preferred embodiment, the DNA sequence gene comprises substantially the human protein C gene from 21 basepairs upstream of the protein C start codon to the NheI site in the 3' end of the protein C gene, or a variant thereof is among the most highly preferred.

In a particularly preferred embodiment, the exogenous DNA sequence comprises a DNA sequence consisting essentially of the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

In accordance with another aspect of the present invention, there has been provided a process for the production of protein C, comprising the steps of (A) providing a transgenic mammal characterized by an exogenous DNA sequence stably integrated in its genome, wherein the exogenous DNA sequence comprises a promoter operably linked to a DNA sequence encoding a polypeptide having protein C activity and a signal peptide, the promoter being specifically active in mammary cells and the signal peptide being effective in directing the secretion of the protein C into the milk of the transgenic mammal; (B) producing milk from the transgenic mammal; (C) collecting the milk; and (D) isolating the polypeptide from the milk.

It is therefore an object of the present invention to provide a transgenic animal which produces in its milk recombinant protein C that comprises a significantly higher percentage of active protein than has been achieved heretofore.

It is another object of the present invention to provide a process for producing protein C in commercially useable amounts, by means of a transgenic mammal.

In accomplishing the foregoing objects, there has been provided, in accordance with one aspect of the present invention, a transgenic mammal containing an exogenous DNA sequence stably integrated in its genome, wherein the exogenous DNA sequence comprises a promoter operably linked to a DNA sequence encoding a polypeptide having protein C activity and a signal peptide, wherein the promoter is specifically active in mammary cells, particularly mammary epithelial cells, and the signal peptide is effective in directing the secretion of the protein C into the milk of the transgenic mammal.

Additionally, in a preferred embodiment the DNA sequence encoding a polypeptide having human protein C activity comprises portions of the non-coding regions of the human protein C gene. In a particularly preferred embodiment of this type the DNA sequence gene comprises substantially the human protein C gene from 21 basepairs upstream of the protein C start codon to the NheI site in the 3' end of the protein C gene, or a variant thereof is among the most highly preferred.

In addition, is certain a particularly preferred embodiment, the exogenous DNA sequence comprises a DNA sequence consisting essentially of the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

In accordance with still another aspect of the present invention, a process has been provided for producing transgenic animals, comprising the steps of (A) providing a mixture containing a genetic construct; (B) subjecting the mixture to anion-exchange high performance liquid chromatography to obtain purified genetic construct; and thereafter (C) microinjecting an aqueous buffer solution containing the purified genetic construct into an animal embryo. In a preferred embodiment, step (B) comprises applying the mixture to an anion-exchange high performance liquid chromatography column, eluting the genetic construct from the column, and then subjecting the genetic construct to a second anion-exchange high performance liquid chromatography.

In a preferred embodiment of this aspect of the invention, the double-stranded DNA is selected from the group consisting of a double-stranded DNA comprising substantially the 5' 4.2 kb Sau3A-Kpn1 promoter fragment of the mouse whey acidic protein promoter, a double-stranded DNA comprising substantially a fragment of the human protein C gene beginning 21 basepairs upstream of the protein C start codon and ending at the NheI site in the 3' end of the protein C gene, and a double-stranded DNA comprising a DNA sequence consisting essentially of the 5' 4.2 kb Sau3A-Kpn1 promoter fragment of the mouse whey acidic protein promoter ligated directly or by a linker to a fragment of the human protein C gene beginning 21 basepairs upstream of the protein C start codon and ending at the NheI site in the 3' end of the protein C gene.

In accordance with yet another aspect of the invention, there has been provided a process for the production of a polypeptide in the milk of a transgenic non-human mammal, comprising the steps of providing a non-human transgenic mammal characterized by an exogenous DNA sequence stably integrated in its genome, wherein said exogenous DNA sequence comprises substantially the 5' 4.2 kb Sau3A-Kpn1 promoter of the mouse whey acidic protein gene, or a variant thereof, operably linked to a DNA sequence encoding said polypeptide and a signal peptide, said promoter being specifically active in mammary cells and said signal peptide being effective in directing the secretion of said polypeptide into the milk of said transgenic mammal; producing milk from said transgenic mammal; collecting said milk; and isolating said polypeptide from said milk. In a particularly preferred embodiment of this aspect of the invention, the exogenous DNA sequence comprises the 5' 4.2 kb Sau3A-Kpn1 promoter fragment of the mouse whey acidic protein promoter.

In accordance with yet another aspect of the invention there has been provided a transgenic non-human mammal containing an exogenous DNA sequence stably integrated in its genome, wherein the exogenous DNA sequence comprises substantially the 4.2 kb Sau3A-Kpn1 whey acidic protein promoter fragment, or a variant thereof, operably linked to a DNA encoding a polypeptide whereby the protein is expressed specifically in mammary cells of the transgenic mammal and the protein comprises a signal peptide, the peptide being effective in directing the secretion of the protein into the milk of said mammal. In a particularly preferred embodiment of this aspect of the invention, the exogenous DNA sequence comprises the 5' 4.2 kb Sau3A-Kpn1 promoter fragment of the mouse whey acidic protein promoter.

In certain preferred embodiments of various aspects of the invention, the transgenic mammal is mouse, rabbit, pig, sheep or goat. In some most highly preferred embodiments the animal is pig or sheep.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 9 shows the nucleotide sequence SEQ ID NO:1 of the WAP gene promoter fragment from the C57B/6 mouse strain. The sequence from the Sau3A site to the KpnI site is shown.

FIG. 10A shows the construction of pWAP4. FIG. 10B shows the production of pUCFIX. FIG. 10C shows the introduction of human FIX cDNA into pWAP4. FIG. 10D shows the production of pUCWAPFIX. FIX cDNA was modified by PCR in order to introduce KpnI sites on the 3' and 5' ends. Using FIX cDNA as a template, PCR primers humFIX5'KpnI and humFIX3'KpnI, as shown in Table 6, below, were used to produce FIX cDNA with KpnI sites on both ends. Modified cDNA may be easily introduced into a "cassette vector" for constructing a chimeric gene.

FIG. 11A shows the production of pUCNotI. FIG. 11B shows the production of of pUCWAP5 and the production of a fragment that contains the pUCNotI vector sequence flanked by mWAP3'UTR. FIG. 11C shows the production of pUCWAP6.

FIG. 16 shows the pUCWAP5 plasmid incorporating a polynucleotide encoding the FIB γ 1 chain.

DETAILED DESCRIPTION OF THE INVENTION

Figure 1:
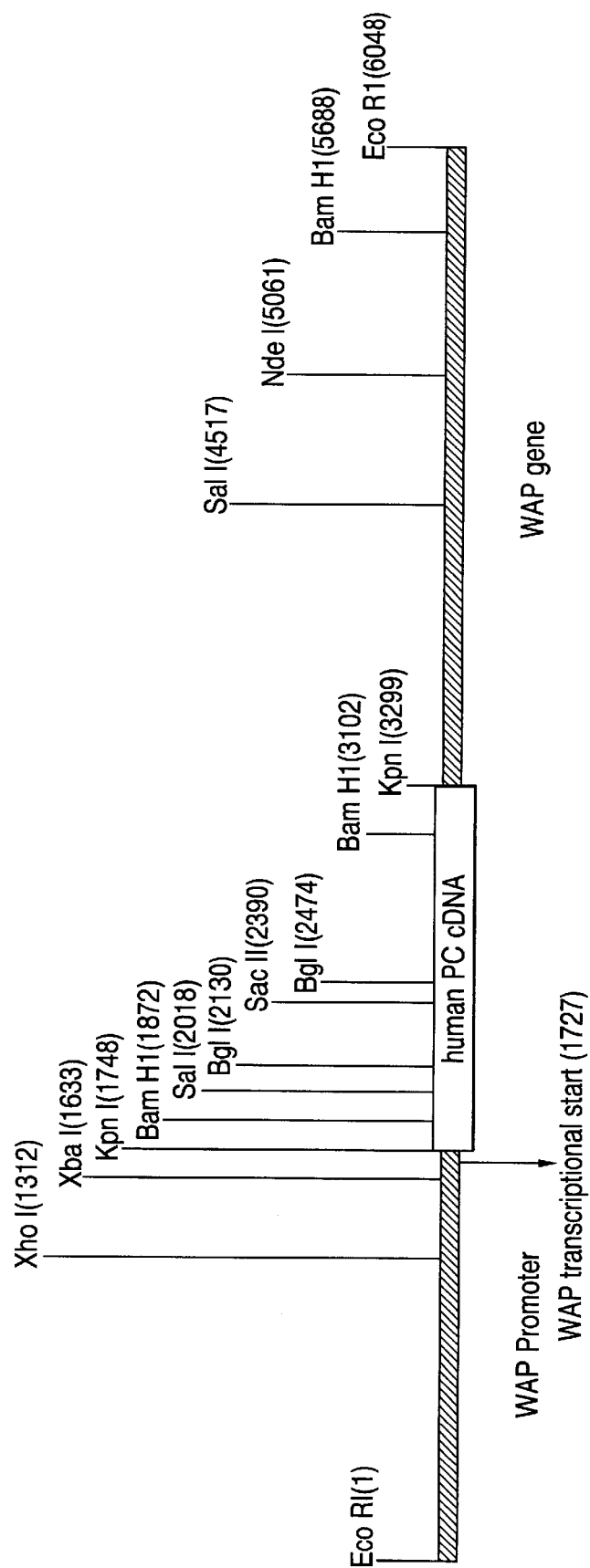
FIG. 1 is a schematic diagram representing WAPpCI, a construct which contains cDNA encoding human protein C inserted into an intact murine whey acidic protein (WAP) gene at the unique Kpn1 site.

Notwithstanding past failures to express heterologous proteins, such as recombinant protein C with suitably high activity in several different expression systems, including transformed mammary cells, it has been discovered that recombinant protein C characterized by a high percentage of active protein can be obtained in the milk of transgenic animals that incorporate DNAs according to the present invention. Transgenic animals of the present invention are produced by introducing into developing embryos DNA that encodes protein C, such that the DNA is stably incorporated in the DNA of germ line cells of the mature animal and inherited in normal, mendelian fashion. In accordance with the invention, DNAs can be introduced into embryos by a variety of means to produce transgenic animals. For instance, totipotent or pluripotent stem cells can be transformed by microinjection, calcium phosphate mediated precipitation, liposome fusion, retroviral infection or by other means. The transformed cells can then be introduced into embryos and incorporated therein to form transgenic animals. In a preferred method, developing embryos can be infected with retroviral vectors and transgenic animals can be formed from the infected embryos. In the most preferred method, however, the DNAs of the invention are injected into embryos, preferably at the single-cell stage, which are allowed to develop into mature transgenic animals.

Suitable protein C-encoding DNA used for producing transgenic animals in this fashion can be obtained using human liver tissue as a source for cloning the hPC gene. The DNA coding for protein C can be fused, in proper reading frame, with appropriate regulatory signals, as described in greater detail below, to produce a genetic construct which is then amplified, for example, by propagation in a bacterial vector, according to conventional practice.

The amplified construct is thereafter excised from the vector and purified for use in microinjection. The purification is preferably accomplished by means of high performance liquid chromatography (HPLC), which rids the construct of contamination from the bacterial vector and from polysaccharides typically present when other techniques, such as conventional agarose electroelution, are used. The preferred HPLC method entails sorbing the construct onto an anion-exchange HPLC support and selectively eluting the construct from the support, preferably with an aqueous sodium chloride solution, thereby to eliminate contamination from the vector. (Elution may be effected by other means, such as a pH gradient.) Alternatively but less preferably, the excised construct can be purified by ultracentrifugation through an aqueous sucrose gradient.

Since it is preferable that the construct have the minimum amount of impurities, more than one cycle of HPLC or other purification is advantageous. In particular, the use of HPLC-purified DNA for microinjection, as described above, allows for remarkably high transformation frequencies, on the order of 20% or more in both mice and pigs. All lactating animals, that is, all mammals, are suitable for use according to the present invention. Preferred mammals include mice, rats, rabbits, pigs, sheep, goats and cows. More particularly, mice, pigs, sheep, goats and cows are preferred. Most preferred at present are mice, pigs and sheep.

DNA constructs useful in the present invention provide a DNA sequence encoding protein C operably linked to all the cis-acting signals necessary for mammary tissue specific expression of protein C, post-translational modification of protein C, secretion of protein C into milk, and full biological activity of protein C.

DNAs useful in the invention include genomic or complementary DNAs that encode naturally occurring protein C. In a preferred embodiment DNAs encoding human protein C are employed, including cDNA and genomic DNAs. DNAs encoding protein C from other species may also be used, such as the protein C encoded by rats, pigs, sheep, cows and chimpanzees.

In a particularly preferred embodiment, human genomic DNAs encoding protein C are employed. Among the most highly preferred human genomic DNAs is the fragment of the human protein C gene beginning 21 basepairs upstream of the protein C start codon and ending at the NheI site in the 3' end of the protein C gene. This fragment, approximately 9.4 kb long, contains regulatory elements that engender high expression of human protein C in the milk of non-human transgenic mammals. Some of these regulatory elements are the AUG start codon, donor and acceptor splice signals, the secretion peptide, and the translation termination, transcription termination and polyadenylation signals.

It will be appreciated that there may be additional regulatory elements in the fragment that aid the production of transgenic non-human mammals that express high levels of protein C in their milk. Some of these signals may be transcription or translation control signals, or those associated with transport out of the cell. Other signals may play a role in efficient chromosomal integration or stability of the integrated DNA. Various regions of the fragment may contain such signals, such as the region between the end of exon VIII and the NheI site in the 3' end of the protein C gene.

It will be readily appreciated that deletional and other mutational techniques may be employed to elucidate further all the signals in this fragment that confer high levels of protein C expression in the milk of transgenic animals.

It will also be appreciated that the 9.4 kb protein C fragment described above can be modified using recombinant DNA techniques in many ways. 3' or 5' portions of the protein C gene can be added, or a few bases at either end may be removed. Introns can be removed or added. Portions of one or more introns can be deleted. Additional DNA can be inserted into them. The sequences of the introns can be altered. Exons can be modified in accordance with the discussion of modified protein C molecules set forth below. Most such modified forms of the preferred genomic protein C fragment will not be significantly changed in their ability in transgenic animals to engender the production of milk-born protein C. Thus, these substantially similar fragments will be equivalent in the invention to the particularly disclosed 9.4 kb fragment of human protein C that begins 21 basepairs upstream of the protein C start codon and ends at the NheI site in the 3' end of the protein C gene.

Modified protein C sequences also can be employed in the present invention. Useful modifications in this context include but are not limited to those that alter the post-translational processing of protein C, that alter the size of protein C, that fuse protein C or portions thereof to portions of another protein, or that alter the active site of protein C. Preferred modifications include those that provide an activated protein C and those that provide for activation of protein C in the absence of thrombomodulin. In a preferred embodiment, modified forms of human protein C are employed.

Such modifications can be introduced into protein C by techniques well known to the art, such as the synthesis of modified genes by ligation of overlapping oligonucleotide, and by introducing mutations directly into cloned genes, as by oligonucleotide mediated mutagenesis, inter alia. The cis-acting regulatory regions useful in the invention include the promoter used to drive expression of the protein C gene. Promoters useful in the invention are active in mammary tissue. Particularly useful are promoters that are specifically active in mammary tissue, i.e., are more active in mammary tissue than in other tissues under physiological conditions where milk is synthesized. Most preferred are promoters that are both specific to and efficient in mammary tissue. By "efficient" it is meant that the promoters are strong promoters in mammary tissue that can support the synthesis of large amounts of protein for secretion into milk.

Among such promoters, the casein, lactalbumin and lactoglobulin promoters are preferred, including, but not limited to the α-, β- and γ-casein promoters and the α-lactalbumin and β-lactoglobulin promoters. Preferred among the promoters are those from rodent (murine and rat), pigs and sheep, especially the rat β-casein promoter and the sheep β-lactoglobulin promoter. The most preferred promoters are those that regulate a whey acidic protein (WAP) gene, and the most preferred WAP promoter is the murine WAP promoter.

A most highly preferred promoter is a mouse whey acidic protein promoter having a length of greater than about 2.4 kb extending upstream from the unique KpnI site in the mouse whey acidic protein gene. A mouse whey acidic protein promoter with a length of approximately 2.4 kb is known as the short WAP promoter. The present invention refers to the short WAP promoter in various locations and in the figures of the present invention as having a length of approximately 2.4–2.6 kb as identified by gel electrophoresis. As is known by persons skilled in the art, this technique provides an approximation of fragment sizes. The size of 2.4–2.6 kb was determined in 1982 and based on methods of gel electrophoresis available at that time. The methods were crude and a band of 2.5 kb, for example, could mean that the fragment is somewhere between 2.3–2.7 kb in size. This short WAP promoter is composed of the EcoRI-KpnI fragment of the mouse whey acid protein promoter. It is now known as a result of nucleotide sequencing by techniques well known to persons skilled in the art that the short WAP promoter is 2410 basepairs in length, and thus the approximate length of 2.4 kb is the correct size designation. This short WAP sequence has been deposited with GenBank and has the Accession No. U38816. Thus, the present invention is intended to encompass a WAP promoter having more than 2410 basepairs. Additionally, the short WAP promoter is described in Gordon et al., *Bio/Technology* 5, 1183–1187 (1987), as having a length of 2.6 kb. This publication is incorporated in its entirety by reference. Thus, the present invention also encompasses a WAP promoter having a length greater than 2.6 kb, as determined by the methods of Gordon et al.

It is the object of the present invention to encompass a mouse whey acidic protein promoter having a length of greater than the short WAP promoter of 2.4 kb in length with this long WAP promoter being responsible for the expression of a heterologous polypeptide at similar or higher levels to that of the Sau3A-KpnI promoter. The promoter expression levels are measureable by persons skilled in the art given the guidance provided in the present application.

A most highly preferred promoter is the 4.2 kb Sau3A-Kpn1 promoter fragment of the mouse whey acidic protein promoter. This promoter fragment is described in detail and the sequence is provided in Paleyanda et al., *Transgenic Research* 3: 335–343 (1994), incorporated herein to disclose inherent properties of the Sau3A-KpnI promoter. The Paleyanda et al. publication refers to this promoter fragment as having a length of 4.1 kb. Again as discussed above, the length as determined by gel electrophoresis is approximate. It is now known as a result of nucleotide sequencing by techniques well known to persons skilled in the art that this Sau3A-KpnI WAP promoter is 4122 basepairs in length, and thus the approximate length of 4.1 to 4.2 kb is the correct size designation. This long WAP sequence was deposited on May 24, 1994 with GenBank and has the Accession No. X79437.

Figure 6:
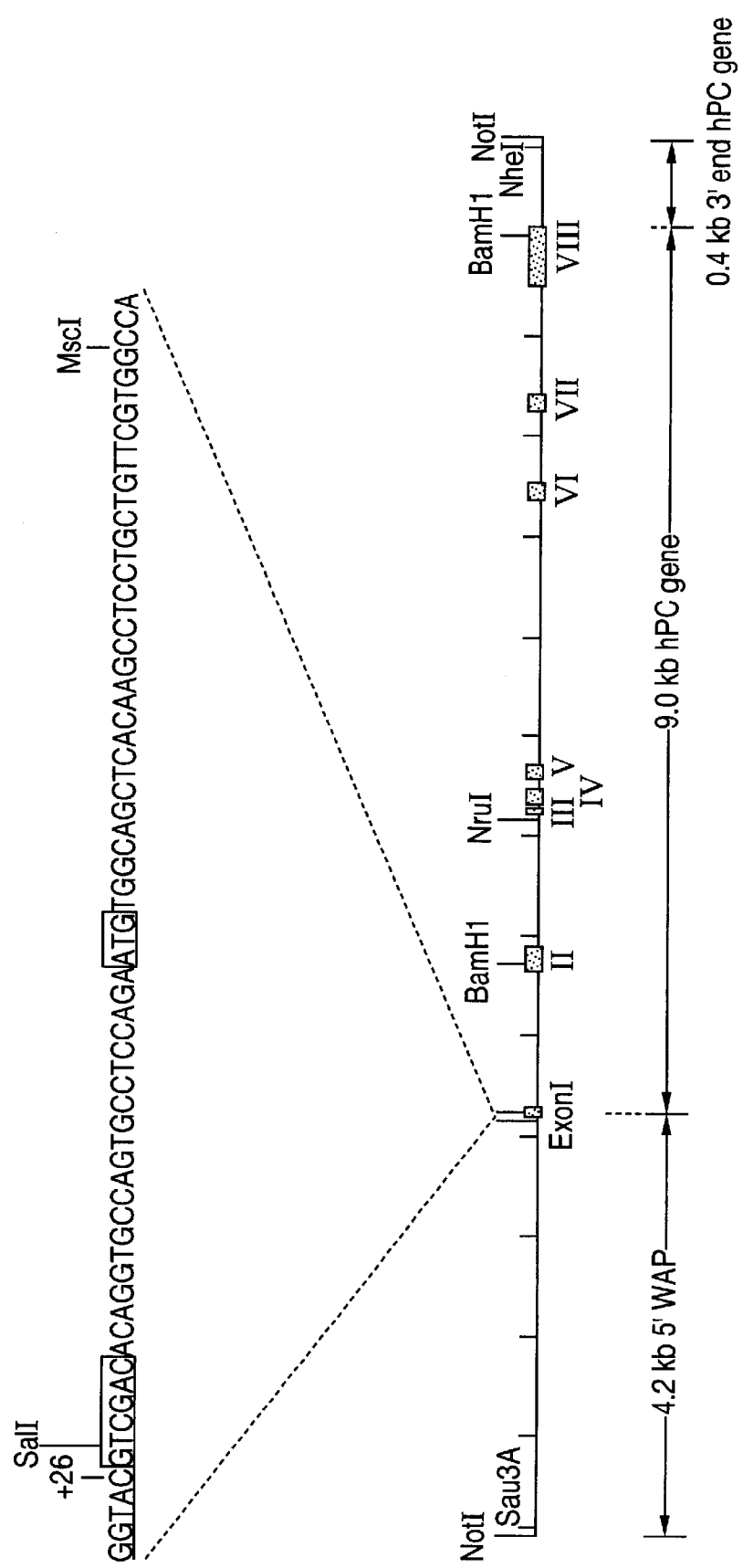
FIG. 6 is a schematic diagram representing a highly preferred murine WAP-human protein C construct. In this construct, a 4.2 kb 5' murine whey acidic protein promoter fragment is linked to a 9.4 kb genomic fragment encoding human protein C which includes the 400 bp extending from the end of exon VIII to the NheI site in the 3' end of the human protein C gene. The sequence of the WAP—hPC junction is shown above the schematic diagram.

The Sau3A-KpnI fragment is also contained within the NotI-KpnI fragment as shown in FIG. 6. This NotI-KpnI fragment containing the Sau3A-KpnI fragment is used to prepare expression constructs for microinjection for the preparation of transgenic mammals. The Sau3A-KpnI fragment is modified at the Sau3A end by the addition of a NotI site to facilitate the preparation of expression vectors. In various locations in the present application, the plasmid pUCWAP6 contains a long WAP promoter with an approximate length of 4.1 kb bounded by NotI and KpnI restrictions sites. The NotI site is part of the plasmid. The NotI-KpnI promoter fragment is 4136 basepairs in length. The present invention is intended to encompass long WAP promoters with these approximate lengths.

It has been found that this fragment is highly efficacious in directing the production of high levels of a protein in the milk of a transgenic animal. In the case of human protein C this mouse whey acidic protein promoter fragment has engendered the production of active protein C in the milk of transgenic animals in concentrations above 4 mg/ml (by polyclonal ELISA).

It also has been found that this long WAP promoter fragment is highly efficacious in directing the production of high levels of polypeptides, particularly blood proteins, such as Factor IX, Factor VIII, human fibrinogen, thrombin, and von Willebrand's factor in the milk of a transgenic animal. In the case of Factor IX, transgenic founder animals have expressed cDNA encoding Factor IX at levels as high as 1500 µg/ml. In the case of human fibrinogen, this mouse whey acidic protein promoter fragment has engendered the production of active fibrinogen in the milk of transgenic animals in concentrations of about 700 µg/ml. See Butler et al., *Thrombosis and Haemostasis*, 78 (1), 537–542 (1997), herein incorporated in its entirety by reference.

It will be readily appreciated, as for the 9.4 kb protein C genomic DNA discussed above, the 4.2 kb Sau3A-Kpn1 whey acidic protein promoter fragment can be modified by recombinant DNA techniques readily available to those of ordinary skill in the art. Thus, the fragment can be shortened, keeping in mind that the 2.4 kb 5' WAP promoter fragment gives rise to very much lower yields. It can be lengthened to include more of the whey acid protein promoter region or other portions of the whey acid protein gene. Portions can be removed, and DNA can be inserted into the fragment. Internal bases can be altered. In the majority of cases these alternatives will not affect the ability of this promoter fragment to induce very high levels of expression. Fragments modified in this way, giving the expected high yields of protein in transgenic milk, are substantially similar variants of the 4.2 kb 5' promoter fragment. They also are useful in the present invention and are functionally equivalent in this respect to the 4.2 kb Sau3A-Kpn1 whey acidic protein promoter fragment itself.

Also important to the invention are the signal sequences that direct secretion of protein into the milk of the transgenic animal. In this regard, both endogenous and heterologous signal sequences are useful in the invention. Generally, the signal peptides of proteins normally secreted into milk are useful in the invention. The signal sequences of proteins that occur in high concentration in milk are particularly preferred, such as the signal peptides of the caseins, lactalbumins and lactoglobulins, including, but not limited to the signal peptides of the α-, β- and γ-caseins and α-lactalbumin and β-lactoglobulin. More particularly, the signal sequence of whey acidic protein is preferred, most particularly the signal sequence of the murine whey acidic protein.

Also particularly preferred are the signal peptides of secreted coagulation factors. Especially preferred in this regard are the signal peptides of protein C, and t-PA. Most especially preferred is the secretion signal of human protein C.

Among the sequences that regulate transcription that are useful in the invention, in addition to the promoter sequences discussed above, are enhancers, splice signals, transcription termination signals and polyadenylation sites, among others. Particularly useful regulatory sequences increase the efficiency of mammary cell specific expression of protein C in transgenic animals. Especially useful in this regard are the other transcription regulatory sequences of genes expressed at high levels in mammary cells, such as the α-, β-and γ-casein genes and the α-lactalbumin and β-lactoglobulin genes mentioned above. Preferred sources for regulatory sequences in this regard are rodents (mice and rats), pigs and sheep. Exemplary of preferred regulatory sequences are those associated with the rat β-casein gene and the sheep β-lactoglobulin gene, respectively. The regulatory sequences most preferred for use in the present invention are those associated with whey acidic protein genes. Particularly preferred in this context are regulatory sequences of the murine whey acidic protein.

Among the sequences that regulate translation, in addition to the signal sequences discussed above, are ribosome binding sites and sequences that augment the stability the protein C mRNA. Especially useful are the translation regulatory sequences of genes expressed at high levels in mammary cells. For instance, the regulatory sequences of the α-, β- and γ-casein genes and the α-lactalbumin and β-lactoglobulin genes are preferred, especially those from rodents (mice and rats), pigs and sheep. Even more particularly preferred are the regulatory sequences of rat β-casein and the sheep β-lactoglobulin genes. The most preferred translational regulatory sequences of the invention are those of the whey acidic protein and the protein C genes. And the most particularly preferred regulatory sequences are those of the murine whey acidic protein and human protein C, including human genomic protein C and human protein C cDNA constructs, and including human protein C cDNA constructs that contain intron sequences. Among these, the most highly preferred are the regulatory sequences of the human protein C gene in the region beginning 21 basepairs upstream of the protein C start codon and ending at the NheI site in the 3' end of the protein C gene, and the regulatory sequences of the mouse whey acidic protein promoter in the 5' 4.2 kb Sau3A-Kpn1 promoter fragment of the mouse whey acidic protein promoter, most particularly when they are used together.

Especially useful in the present invention are sequences that advantageously modulate post-translational modifications of protein C, such that the protein C produced in the transgenic animals of the invention is active. In particular, the genomic sequences of the human protein C gene are preferred. Thus, in accordance with the present invention a DNA sequence that encodes protein C is operably linked to cis-acting regulatory sequences which allow for efficient expression of protein C in milk. The resulting chimeric DNA is introduced into a mammalian embryo, where it integrates into the embryonic genome and becomes part of the heritable genetic endowment of all the cells, including the germ line cells, of the adult which develops from the embryo. The protein C which is expressed in the mammary tissue and secreted into the milk of a transgenic mammal obtained in this manner displays a surprisingly high percentage of active protein, as measured by enzymatic and coagulation-inhibition assays which are conventionally employed to detect protein C activity, such as ELISAs, chromogenic activity assays and coagulation inhibition assays. Levels of active protein on the order of 80% to 90% or more are characteristic of the protein C expressed in accordance with the present invention. Obtaining milk from a transgenic animal within the present invention is accomplished by conventional means. McBurney et al., *J. Lab. Clin. Med.* 64: 485 (1964). The protein C contained in such milk can be purified by known means without unduly affecting activity. One suitable approach to purification in this regard is immunoaffinity chromatography. Alternatively, the expressed protein C can be isolated from the milk by other conventional means, for instance, by the method of Kisiel, *J. Clin. Invest.* 64: 761 (1979). In any event, it is preferred that protein C produced in milk pursuant to the present invention should be isolated as soon as possible after the milk is obtained from the transgenic mammal, thereby to mitigate any deleterious effect(s) on the stability of the protein.

The present invention is further described by reference to the following, illustrative examples.

EXAMPLE 1

DNAs Useful for Expressing Protein C in Transgenic Animals

The entire murine WAP gene including 2.5 kb of 5' untranslated sequence and 3' untranslated regions was cloned by standard methods. See Campbell et al., *Nucleic Acids Res.* 12: 8685 (1984). The human placental cDNA for human protein C was obtained from C. Shoemacker. Human genomic DNAs encoding protein C were cloned by standard methods from a human placental genomic library. The 9.4 kb fragment was assembled from two genomic clones and a SalI, MseI ended 60 bp synthetic oligonucleotide that was added to the 5' end of the gene.

Standard recombinant DNA techniques were employed to generate the vectors and expression constructs of the preferred embodiments, and for other manipulations of DNA, as set forth below. See Sambrook et al., MOLECULAR CLONING, A LABORATORY MANUAL, Vol. 1–3 (Cold Spring Harbor Press 1989).

(1) WAPpC1

A DNA construct called WAPpC1 was made, consisting of the entire murine WAP gene containing one copy of human protein C cDNA inserted at the unique KpnI site, 24 base pairs 3' of the transcriptional start site of the WAP gene (FIG. 1). This WAP-protein C construct was ligated into a bluescribe vector (Stratagene) to facilitate further manipulation.

(2) WAPpC2

WAPpC2 is similar to WAPpC1, comprising the entire murine WAP gene and human protein C cDNA but differs from WAPpC1 in lacking artefactual 5' flanking sequences present in WAPpC1 as a result of cloning procedures used to make that construct. Specifically, 33 bp 5' to the protein C ATG and 118 "A's" at the 3' end of the protein C cDNA were removed by PCR, and new KpnI sites were added at the 5' and 3' ends.

EXAMPLE 2

Preparation of DNAs for Microinjection

DNA for microinjection was prepared according to the procedures described below for DNA from WAPpC1.

The 9 kb WAPpC1 fragment was removed from the vector with the restriction enzyme EcoRI. After digestion with EcoRI the solution containing the WAPpC1 DNA was brought to 10 mM magnesium, 20 mM EDTA and 0.1% SDS and then extracted with phenol/chloroform. DNA was precipitated from the aqueous layer with 2.5 volumes of ethanol in the presence of 0.3 M sodium acetate at −20° C. overnight. After centrifugation, the pellet was washed with 70% ethanol, dried, and resuspended in sterile distilled water.

DNA for microinjection was purified by HPLC. The digested DNA was precipitated with isopropanol and then dissolved in TE buffer at 0.3 μg/ml. Fragments were purified by HPLC using a Waters GEN FAX PAC HPLC column. The column was run isocratically using a buffer consisting of 25 mM Tris-HCl (pH 7.5), 1 mM sodium EDTA, and 0.63 M NaCl. This is the minimum NaCl concentration that will elute the large construct fragment and results in the best resolution from the smaller vector fragment which elutes just prior to the construct fragment. About 15 μg of digested DNA was loaded on the column at a time. The construct-fragment samples from all of the chromatographic runs were then pooled, reprecipitated, and run through the column a second time. Results reported below, for both pigs and mice, were generated using HPLC-purified DNA.

DNA concentrations were determined by agarose gel electrophoresis by staining with ethidium bromide and comparing the fluorescent intensity of an aliquot of the DNA with the intensity of standards. Samples were then adjusted to 10 μg/ml and stored at −20° C., prior to microinjection.

EXAMPLE 3

Transgenic Animals (1) Mice

Transgenic mice were produced essentially as described by Hogan et al., MANIPULATING THE MOUSE EMBRYO (Cold Spring Harbor Press 1986). The procedures employed are outlined below.

Glass needles for micro-injection were prepared using a micropipet puller and microforge. Injections were performed using a Nikon microscope having Hoffman Modulation Contrast optics, with Narashigi micromanipulators and a pico-injector driven by $N_2$ (Narashigi). Fertilized mouse embryos were surgically removed from the oviducts of superovulated female CD-1 mice and placed into M2 medium. Cumulus cells were removed from the embryos with hyaluronidase at 300 µg/ml. The embryos were then rinsed in new M2 medium, and transferred into M16 medium for storage at 37° C. prior to injection.

After injecting the DNA solution into the male pronucleus, embryos were implanted into avertin-anesthetized CD-1 recipient females made pseudo-pregnant by mating with vasectomized males. Embryos were allowed to come to term and the newborn mice were analyzed for the presence of the transgene as described below.

(2) Pigs

Embryos were recovered from the oviduct. They were placed into a 1.5 ml microfuge tube containing approximately 0.5 ml embryo transfer media (phosphate buffered saline +10% fetal calf serum, Gibco BRL). These were then centrifuged for 12 minutes at 16,000×g RCF (13,450 RPM) in a microcentrifuge (Allied Instruments, model 235C). Embryos were removed from the microfuge tube with a drawn and polished Pasteur pipette and placed into a 35 mm petri dish for examination. If the cytoplasm was still opaque with lipid such that pronuclei are not visible, the embryos were centrifuged again for 15 minutes. Embryos to be microinjected were placed into a microdrop of media (approximately 100 µl) in the center of the lid of a 100 mm petri dish. Silicone oil was used to cover the microdrop and fill the lid to prevent media from evaporating. The petri dish lid containing the embryos was set onto an inverted microscope (Carl Zeiss) equipped with both a heated stage and Hoffmnan Modulation Contrast optics (200×final magnification). A finely drawn (Kopf Vertical Pipette Puller, model 720) and polished (Narishige microforge, model MF-35) micropipette was used to stabilize the embryos while about 1–2 picoliters of HPLC-purified DNA solution containing approximately 200–500 copies of DNA construct was delivered into the male pronucleus with another finely drawn micropipette. Embryos surviving the microinjection process as judged by morphological observation were loaded into a polypropylene tube (2 mm ID) for transfer into the recipient pig.

(3) Other Animals

Methods for microinjection of other animal species are similar to the methods set forth above.

EXAMPLE 4

Assessment via PCR of WAP/hPC Constructs in Transgenic Animals (1) Preparation of DNA Form Transgenic Animals DNA can be prepared from tissue of a transgenic animal of any species by the method exemplified below for mice.

A 5 mm piece of mouse tail was removed from young, potentially transgenic mice at weaning (3 weeks of age), minced, and treated with proteinase K and SDS at 37° C. overnight. The mixture was then incubated with DNase-free RNase at 37° C. for 1–2 hours. DNA was precipitated from the mixture with sodium acetate and ethanol at −20° C. overnight, collected by centrifugation, washed in 70% ethanol and dried. The dried DNA pellet was used directly for PCR. In some cases the mixture was extracted extensively with phenol/chloroform prior to ethanol precipitation.

Essentially the same technique was used to prepare DNA from pigs, and the same or similar techniques can be used to prepare DNA from other animals.

(2) Oligonucleotide Probes Used in the PCR Assay

Figure 2:
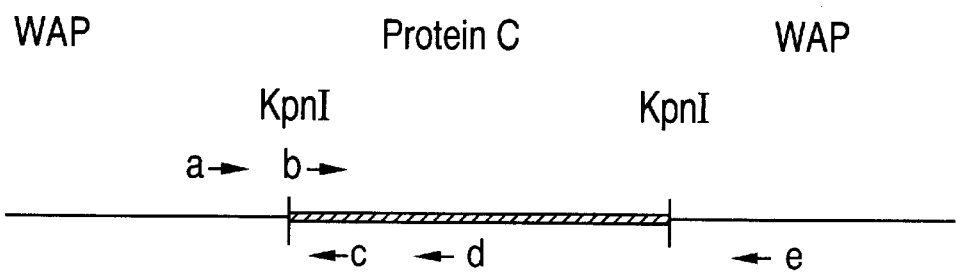
FIG. 2 is a schematic representation of polymerase chain reaction (PCR) primer pairs useful to detect WAP-protein C DNAs in transgenic animals.

Oligonucleotide pairs were used to prime polymerase chain reactions that detected the presence of WAP-protein C constructs in the transgenic animals. These pairs and their extension products are shown schematically in FIG. 2. Oligonucleotide pairs that bridge the region from the WAP sequences 5' of the KpnI site and the endogenous WAP sequences which naturally lie 3' of the KpnI site also provided positive controls in mice.

(3) PCR Reaction Conditions and Product Analysis

PCR reactions were performed using an annealing temperature of 58° C., a denaturation temperature of 94° C., and an extension temperature of 72° C., using 100 ng of oligo primers and 50 ng of (genomic) template DNA per reaction, and cycling through the temperatures 40 times using an automatic temperature cycler (M.J. Research).

PCR reactions were analyzed by running 20% of the reaction products on agarose gels and identifying fragment sizes by comparison with marker DNA fragments.

(4) Results of PCR Analysis of Transgenic Animals

PCR analysis of potentially transgenic mice and pigs which developed from embryos microinjected with WAPpC1 and WAPpC2 constructs are summarized in Table 2. The results show that WAPpC constructs frequently integrated into the embryonic genomes of both mice and pigs. Furthermore, mendelian transmission was observed in 5 of the 16 mice which were tested.

TABLE 2

Whey Acid Protein-Protein C Construct Integration Rates

| Animal | # Tested | # Positive | Integration Rate |
| --- | --- | --- | --- |
| Mice | 105 | 30 | 29% |
| Pigs | 23 | 5 | 22% |

Mendelian Transmission in Transgenic Mice 5/16 Tested = 31%

EXAMPLE 5

Preparation of Milk and Whey from Transgenic Animals

Lactating mice were milked an average of 3 times per week. The mice were first separated from their young for approximately 5 hours. They were then anesthetized with 0.4 ml avertin at 2.5% (I.M.), and 0.2 ml oxytocin was then administered at 2.5 IU/ml (I.P.) to permit release of the milk. A milking device consisting of a vacuum pump (2.5 psi) and syringe with an eppendorf tip was used to direct milk into an eppendorf tube. During collection, milk was placed on ice until all samples were obtained.

To prepare whey, milk was diluted 1:1 with TS buffer (0.03 M Tris pH 7.4; 0.06 NaCl) and centrifuged in a TLA-100 rotor in a Beckman TL-100 table top ultracentrifuge at 51,000 rpm (89,000×g) for 30 minutes at 4° C. After centrifugation the tubes were put on ice, and the whey was collected with an 18 gauge needle, leaving the casein pellet and upper cream layer in the tube. To remove solids or cream that co-transferred during the initial recovery, the whey obtained from the first centrifugation was subjected to a second spin at 12,000 rpm for 30 minutes at 4° C. in a TMA-4 rotor in a Tomy MTX-150 centrifuge. Following the second spin the tubes were place on ice and the whey was recovered as before.

EXAMPLE 6

Determination by ELISA of Protein C Produced by Transgenic Mammals

An ELISA was used to measure the amount of protein C protein produced by transgenic animals in their milk or whey. Two monoclonal antibodies, 7D7B10 and 12A8, and a polyclonal antiserum were used in the ELISAs, and a variety of other protein C specific antibodies could be employed. The 7D7B10 monoclonal is specific for the $NH_2$ terminus of the light chain of protein C. 12A8 is specific for the reactive site on the heavy chain of protein C. Microtiter plate wells were coated overnight at 4° C. with 3 µg/ml of monoclonal antibody in 50 µl of 0.1 M sodium bicarbonate buffer, pH 8.3. The wells were washed once with TET buffer (0.01 M Tris pH 7.5; 0.01 M EDTA; 0.02% tween-20, pH 7.45) and then blocked with 1% BSA in PBS using 400 µl per well for 1 hour at 37° C. Plates were again washed with TET buffer (5x) followed by addition of 100 µl of sample whey or normal whey spiked with human protein C from plasma, to generate a standard curve. After washing 5x with TET buffer, horse radish peroxidase (HRP)-conjugated to rabbit anti-hPC was diluted 1:1000 in 0.1% BSA/TET and 100 µl was added per well and incubated for 2 hours at room temperature, with shaking at 100 rpm. After again washing 5 times with TET buffer, 100 µl of orthophenyldiamine (OPD), from a stock solution made by dissolving one tablet of OPD in 20 ml of 0.1 M citrate-phosphate buffer (pH 5.0), were added to each well. After 10 minutes at room temperature the reaction was stopped with 1 N sulfuric acid. The extent of the reaction was determined by measuring product absorption at 490 nm.

Figure 3:
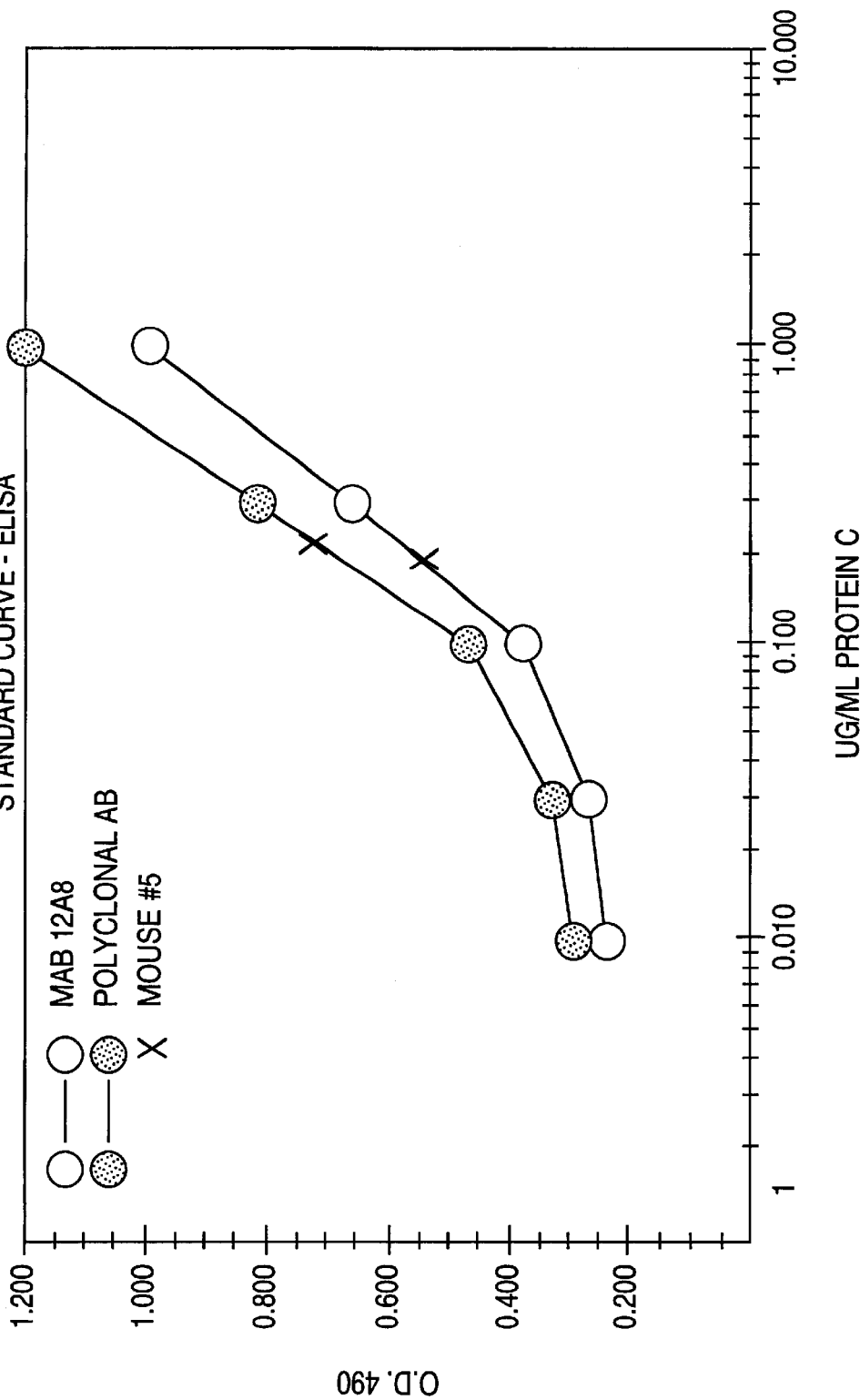
FIG. 3 is a graph that shows the results of an enzyme linked immunosorbent assay (ELISA) of human protein C in milk obtained from a transgenic mouse.

The result of an ELISA analysis of the milk from one transgenic mouse (Mouse No. 5) is shown in FIG. 3. Standard curves were obtained for a monoclonal antibody, 12AB, and a rabbit polyclonal antibody, tittered against human protein C which was obtained by immunoaffinity chromatography over immobilized 7D7B10 antibody. The milk sample, taken from transgenic Mouse No. 5, contained approximately 200 ng/ml protein C.

To assure proper protein C structure as judged by immunocapture by two different monoclonal antibodies, as well as by a polyclonal mixture of antibodies, the samples for several different transgenic mice were screened by ELISAs. Table 2A shows essentially equivalent antigen levels, as judged by three different immunocaptures and detection by ELISA. The majority of mice produced by microinjection of WAPpC1 produced antigen levels in the 1-to-4-µg/ml range.

TABLE 2A hPC ANTIGEN ELISA (NG/ML)

| MOUSE ID-DAY | MONOCLONAL LC-CAPTURE | MONOCLONAL HC-CAPTURE | POLYCLONAL CAPTURE |
|---|---|---|---|
| Y52-15 | 1820 | 3530 | 4100 |
| Y57-15 | 930 | 1150 | 2880 |

The concentration of human protein C in whey obtained from transgenic mice, as well as milk, was also determined in this manner, with equivalent results.

Similar assays were routinely carried out to assay protein C in milk obtained from transgenic animals. Results obtained using the 7D7B10 antibody in light-chain capture ELISAs are compiled in Table 3, which summarizes the concentration of protein C in milk obtained from transgenic mice during the first four lactation periods. Dashes indicate that no test was done. All of the animals provided significant levels of protein C in their milk. Preliminary results also indicate that the second lactation period is sometimes superior to the other periods tested.

TABLE 3 hPC ELISA SCREENING (LIGHT CHAIN CAPTURE)

| | PC-Ag (µg/ml) Day of Lactation | | | |
|---|---|---|---|---|
| MOUSE ID | 5–6 | 8–9 | 11–12 | 13–15 |
| Y68-L2 | — | 1.05 | — | — |
| Y51-L2 | — | 1.08 | — | 0.56 |
| Y51-L3 | — | 2.80 | 1.30 | 1.79 |
| Y52-L1 | — | 0.55 | 0.65 | — |
| Y52-L2 | — | 1.52 | — | 0.95 |
| Y57-L1 | — | — | 0.52 | 1.35 |
| Y57-L2 | 1.47 | — | 0.98 | — |
| R03-L2 | 1.90 | 2.88 | 3.01 | — |
| R12-L1 | — | 0.60 | — | — |
| R12-L2 | — | 2.98 | 2.48 | 2.40 |

Human protein C in the milk obtained from other species can be measured by the same methods. Thus, protein C from human plasma spiked into pig milk was accurately detected via the above-described ELISA.

EXAMPLE 7

Assay for Protein C Amidolytic Activity Using the Chromogenic Substrate S-2366

(1) Microtiter Well Assay

The enzymatic activity of protein C in the milk of transgenic animals was measured directly using a chromogenic assay essentially as described by Odegaard et al., *Haemostasis* 17: 109 (1989). In this assay microtiter plate wells were coated with the 7D7B10 monoclonal antibody (50 µg/ml) in 50 µl of 0.1 M bicarbonate buffer, pH 8.6 at 4° C. overnight. Plates were then rinsed with TET buffer (0.1 M Tris; 0.03 M EDTA; 0.05% tween-20) and blocked with 400 µl/well 1% BSA in PBS and incubated at room temperature for 1 to 1.5 hours. After rinsing 3 times with TET buffer, 50 µl of whey sample and 50 µl of 0.1 M Tris pH 7.5, 0.03 M EDTA was added per well and incubated at room temperature for 2 hours. Plates were washed 3 times in TET buffer. The captured human protein C was activated by adding 120 µl of Protac™, a commercial reagent containing a snake-venom enzyme (12 ml distilled water per vial), 30 µl TSP buffer and 0.1% BSA, pH 7.5, per well. After incubation for 6–10 minutes at room temperature, 120 µl S-2366 (Kabi substrate) at 25 mg/10.8 ml Tris pH 7.8 was added to each well and the plates were incubated for 2–8 hours at room temperature, or several days at 4° C. The amount of protein C activity in each sample was determined by measuring formation of the reaction product by absorption at 405 mm.

Results obtained using milk and whey from a transgenic mouse and the pooled milk and whey of several transgenic mice appear in Table 4, which shows the amount and the specific activity of protein C in the samples. Note that the samples were obtained either during the first lactation period, L1, or were obtained from a second and third lactation, L2 and L3. The specific activity of the human protein C obtained from transgenic mice determined in these assays, 205 units (U) per mg, is similar to that of human protein C of similar purity obtained from natural sources. (A "unit" is defmed by pooling blood from many individuals and determining activity in 1 ml of the pooled blood.)

TABLE 4

Protac ™ -Specific Amidolytic Activity Upon S-2366

|  | U/ml | μg Ag/ml | U/mg |
|---|---|---|---|
| Reconstituted Whey Y52-L1 Pool* | 0.07 | 0.34 | 206 |
| Y52-L1 Milk Pool* | 0.23 | 1.12 |  |
| Transgenic Whey Pool** | 1.12 | 0.55 | 205 |
| Transgenic Milk Pool** | 0.43 | 2.10 |  |

*Pooled milk from day 5–15.
**L2 and L3 from mice Y51, Y52, Y57, R03, R12.

(2) Amidolytic Activity Assay on Nitrocellulose

Whey proteins were resolved by electrophoresis through polyacrylamide gels under non-reducing conditions in the presence of SDS. Following electrophoresis proteins were transferred out of the gel and immobilized on a nitrocellulose membrane by electroblotting. SDS was removed from the membrane by thorough washing in 0.05 M Tris-Cl, 0.175 M NaCl, 0.25% Triton X-100, pH 8.0, and the membrane was then equilibrated in 0.25 M Tris-Cl pH 8.0. Following equilibration the membrane was incubated in Protac C, 0.25 U/ml in distilled water. A 1% agarose indicator gel in 25 mM Tris-Cl pH 8 containing 1 mM chromogenic substrate S-2366 was then placed onto the gel, and the filter and gel overlay were incubated under moist conditions for 30–90 minutes at 37° C. Colored bands generated by protein C activity on the filter were visualized under U.V. light, and photographed.

Figure 8A:
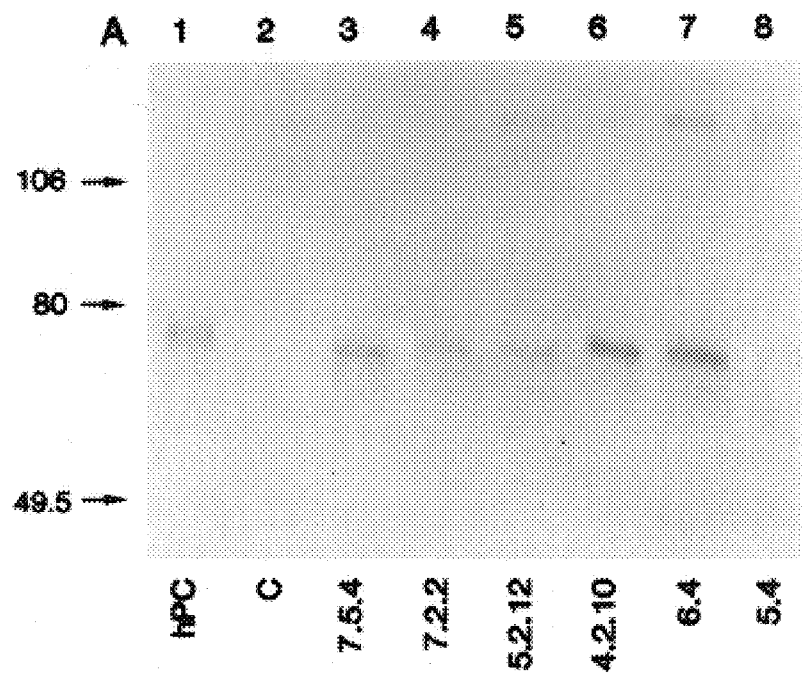
FIG. 8 shows the amidolytic activity in samples of whey from transgenic mice. Panel A shows amidolytic activity of whey proteins resolved by PAGE under native conditions. Panel B shows the proteins detected by anti-hPC antibodies in a western blot of an identical gel, visualized using 4-chloro-1-naphthol. Lanes were loaded with approximately 50 μg of protein. Lane 1 contained purified human protein C. Lane 2 contained a sample form a non-transgenic mouse. Lanes 3 through 8 contained, respectively, samples from transgenic mice 7.5.4, 7.2.2, 5.2.12, 4.2.10, 6.4 and 5.4.
Figure 8B:
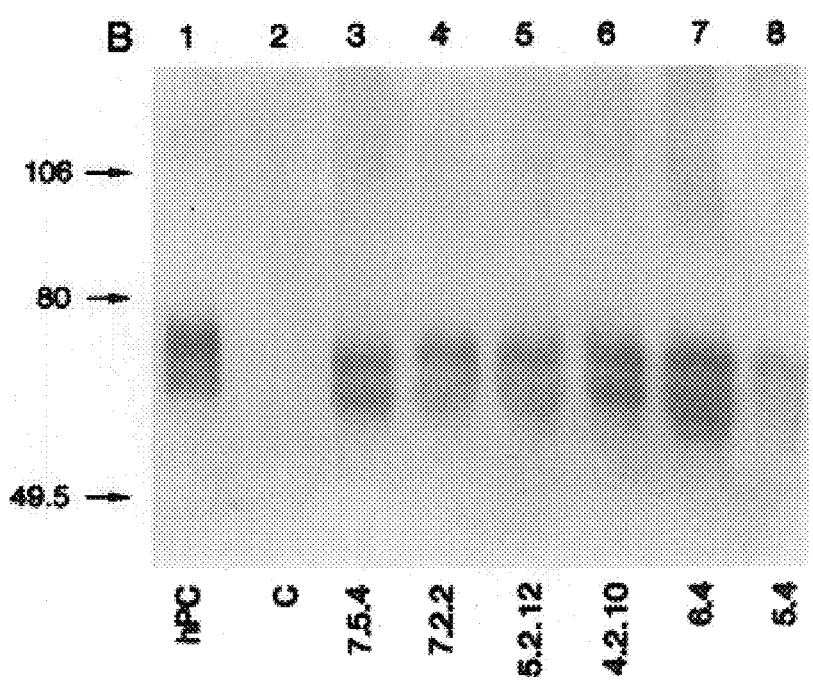

FIG. 8 shows the results obtained by this assay for milk produced by transgenic mice that were stably transformed with a double stranded DNA comprising the 5' 4.2 kb WAP promoter ligated via a linker to the 9.4 kb human genomic protein C fragment. All of these transgenic mice produced amidolytically active protein C in their milk, giving rise in the blots to a strong band and a weak band of amidolytic activity (FIG. 8, panel A). Notably, bands of the same migration were detected in each whey sample when a similar blot was probed with an anti-protein C antibody (FIG. 8, panel B).

EXAMPLE 8

Determination of Protein C Produced in Transgenic Mammals by Activated Partial Thromboplastin Clotting Time Assay The activity of protein C was also measured in a clotting time assay, the activated partial thromboplastin clotting time assay (APTT). In this assay, each well of a plastic Coag-a-mate tray received 90 μl of PC-deficient plasma plus 10 μl of an APC standard or unknown, diluted with Tris/saline/BSA. The tray was then placed on an automated analyzer (APTT mode, 240 second activation). The run was started, which automatically performed the addition of 100 μl of APTT reagent and 100 μl of 0.025 M $CaCl_2$. Data obtained using a standard APC preparation was fitted to the equation y−ax+b where y=clotting time and x=APC, which was then used to determine the amount of APC in a sample.

Figure 4:
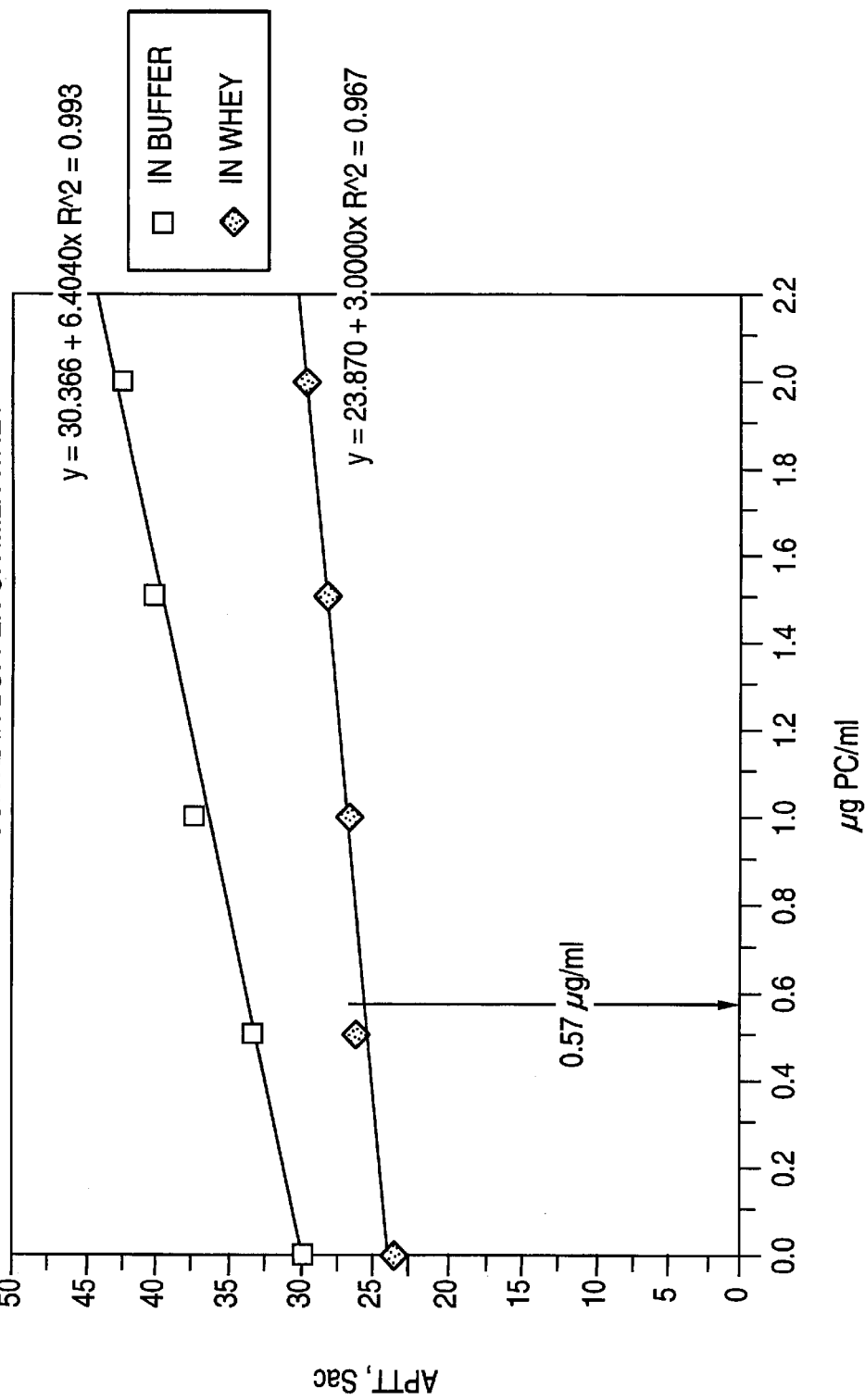
FIG. 4 is a graph that shows the results of an APTT assay to determine human protein C anti-coagulant activity in whey obtained from a transgenic mouse.
Figure 5:
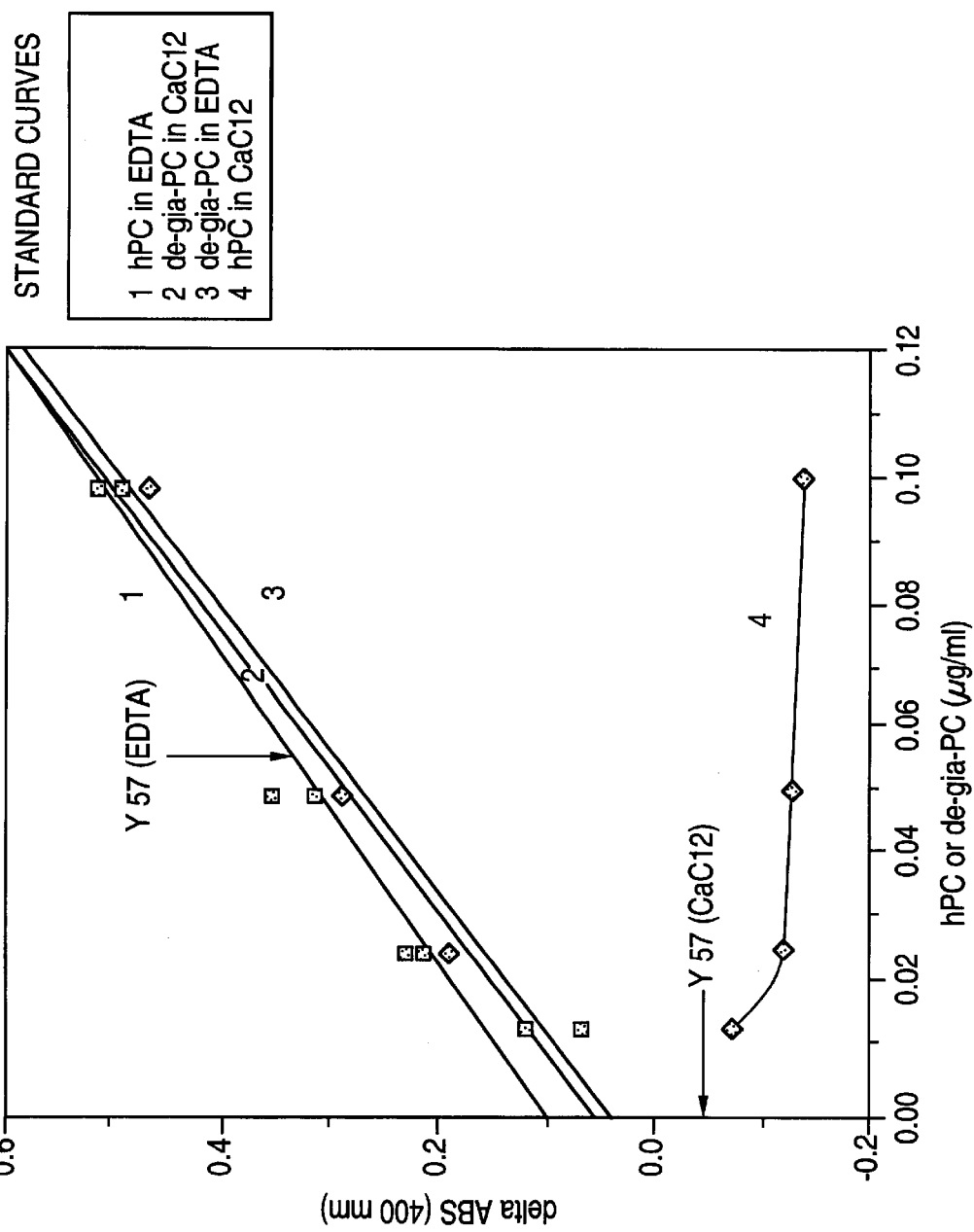
FIG. 5 is a graph that shows the results of $Ca^{2+}$-dependent and $Ca^{2+}$-independent light chain capture ELISAs which demonstrate that the γ-carboxyglutamic acid in human protein C in whey from transgenic mouse Y52 is similar to that in protein C derived from human serum.

The result of an APTT assay of whey pooled from transgenic mice is shown in FIG. 4. The standard curves in the figure correlate the activity determined by the APTT assay with the amount of active human protein C in mouse milk or mouse whey. The activity in the APTT assay of the whey sample obtained from the transgenic mouse corresponded to a concentration of approximately 0.57 μg/ml, interpolated from the standard curve for human protein C in whey. An ELISA (not shown) of the same whey sample detected approximately 0.60 μg/ml of human protein C, as protein. Thus, within the normal range of error of these assays, human protein C produced in transgenic mice is as active as the control human protein C.

EXAMPLE 9

Mapping of Calcium Dependent Conformer by Metal-Dependent Immunoaffinity

Standard ELISAs were run in normal mouse milk whey with varying concentrations of hPC or hPC without Gla regions in the presence of 25 mM EDTA. After capture by 7D7B10, an assay replicating that effected with 25 mM EDTA was treated with several washes of 25 mM $CaCl_2$, and then was followed by the ELISA detection protocol described previously. While de-Gla protein remained bound to the capture antibody in the presence of $CaCl_2$, the PC standard did not remain bound in the presence of added $CaCl_2$. It was observed that whey from the transgenic mouse Y57 behaved in a similar manner to the γ-carboxylated native PC, suggesting that it is also γ-carboxylated like the native molecule.

EXAMPLE 10

Purification of Human Protein C from the Milk of Transgenic Animals (1) Preparation of Whey Samples Milk from several WAPpC1 transgenic mouse lines was pooled, chilled on ice, diluted 6-fold with 50 mM Tris-HCl, 0.15 M NaCl pH 7.2 (TBS) (1 ml milk per 5 ml TBS), and centrifuged at 125,000×g for 30 minutes at 4° C. Following centrifugation, the whey was collected and pooled using a pasteur pipet and pooled, being careful not to disturb the fatty overlayer or the casein pellet. Samples were removed from the pool for later assay and then both the samples and the pooled whey were frozen and stored at −90° C. Human protein C in samples was determined by ELISA, as described above.

Individual whey pools were thawed at 2° C.C, combined, and the amount of human protein C (hPC) in the combined pool was determined by ELISA using the 7D7B10 monoclonal antibody (Mab). The combined pool contained approximately 30 μg hPC, determined by this assay, which was within 20% of the total determined by adding determinations of the individual pools.

The combined pool, approximately 150 ml, was dialyzed (14,000 MW cutoff) against 25 mM EDTA-TBS diluted 5-fold with pure water. The dialyzed whey was concentrated 5-fold by lyophilization and subsequent reconstitution with nanopure water, to yield a final buffer concentration equivalent to 25 mM EDTA in TBS, and a 5-fold increase in protein concentration. The concentrated whey contained 930 mg protein, as estimated by optical absorption at 280 nm, at 16 mg/ml.

2) Immunoaffinity Chromatography

The resin immunosorbent (Affiprep™) used to purify human protein C in the whey of transgenic mice contained 3.3 mg 7D7B10 Mab/ml of Affiprep resin. The 7d7B10 Affiprep resin was assessed by mock immunopurification using 30 μg of plasma derived hPC doped into control (nontransgenic) mouse whey. Approximately the same relative amount of total protein was loaded onto the column (660 mg on a 10 mL Affiprep) and otherwise processed as described below.

Freshly concentrated whey (16 mg/ml, 930 mg total protein, as determined by optical absorption at 280 nm) was batch-loaded onto 13 ml of 7D7B10 Affiprep containing 3.3 mg 7D7B10 Mab/ml resin for 4 hours at 2° C., without addition of carrier protein. The column was fresh and the high total (background) protein loading was thought to be enough to condition the column. The resin was then loaded into a 1 cm diameter column and washed with 25 mM EDTA-TBS until baseline optical density (O.D.) was detected at 280 nm (3 column volumes to obtain <0.0005 O.D.)

The column was then eluted with 25 mM $CaCl_2$ in TBS pH 7.2, followed by 100 mM $CaCl_2$ in TBS, followed by 4 M NaCl, followed by 2 M Na thiocyanate at 0.5 ml/min. The column was re-equilibrated with 5 column volumes of 25 mM EDTA-TBS, 0.02% sodium azide.

All peak pools were dialyzed in a 100-fold dilution (by nanopure water) of 50 mM imidazole, 0.1 M NaCl buffer using a 14,000 MW cutoff dialysis tubing, then lyophilized, then reconstituted to 50 mM imidazole, 0.1 NaCl buffer strength using nanopure water resulting in a 100-fold concentration of protein.

Samples of these eluate pool concentrates were prepared as per the method of Laemmli (1970), applied to a 15 well, 9 cm×2 cm, 4% stacking gel above a 7.5 cm, 7.5% resolving (30%: 2.7% bis) sodium dodecylsulphate polyacrylamide gel and electrophoresed (SDS-PAGE). After electrophoresis, the gel was stained with 1.25% Coomassie Blue dye solution.

The area of the eluate peaks obtained from immunopurification of whey from WAPpC1-transgenic mice was found to be very similar to the mock trial using an equivalent amount of (plasma derived) hPC-doped whey from control mice. Assay of 100-fold concentrated 25 mM $CaCl_2$ eluate product from WAPpC1 transgenics showed 40% yield based upon densitometry of SDS-PAGE stained with Coomassie Blue (yield not determined for mock purification). The total peak areas from mock- and WAPpC1-whey were approximately the same for all eluate peaks including the 2 M Na thiocyanate peak. Approximately 2 µg of hPC antigen (ELISA with immunocapture using 7D7B10 Mab) was detected in the column fallthrough which had been combined with EDTA-TBS wash. Approximately 14 µg of hPC was detected in the 25 mM $Ca^{2+}$ eluate pool, less than 0.1 µg hPC antigen in the 100 mM $Ca^{2+}$ eluate pool, no hPC antigen was detected in the 4 M NaCl pool, approximately 10 µg of hPC was detected in the 2 M Na thiocynate eluate pool. Thus, 87% of the hPC antigen applied to the column was accounted for in the total antigen recovered from column effluents. A 47% antigen yield was obtained based upon the hPC antigen recovered in the 25 mM $Ca^{2+}$ eluate peak.

The starting whey applied to the column, the 2 M sodium thiocyanate eluate, the 25 mM $Ca^{2+}$ eluate product, and a reference hPC derived from plasma by the American Red Cross (Lot #28300277, supplied by Dr. Carolyn Orthner) were analyzed by SDS-PAGE, both reduced and non-reduced. The 2 M sodium thiocynate and 25 mM $Ca^{2+}$ eluate pools were concentrated as described above and 4 µg of antigen applied to the gel for each lane. The immunopurified hPC reference was applied to the gel as 4 µg total protein based upon O.D. at 280 nm. Scanning densitometry of this reference hPC indicated that the sample was greater than 99% pure on nonreduced SDS-PAGE, and 71% pure on reduced SDS-PAGE. Subsequent antigen assays performed on the hPC reference material indicated the concentration of the sample to be such that only 2.7 µg of the reference sample was applied to the gel. The 25 mM $Ca^{2+}$ eluate product is greater than 94% pure based upon non-reduced SDS-PAGE and 86% pure based upon reduced SDS-PAGE. The staining intensity of the 25 mM $Ca^{2+}$ eluate lanes is consistent with our previous experience for 4 µg antigen applications. The bands corresponding to reference hPC possessed lighter intensity relative to the 25 mM $Ca^{2+}$ eluate. A slightly split band at approximately 62,000 relative molecular weight (Mr) is seen for both the non-reduced reference hPC and the 25 mM $Ca^{2+}$ eluate. A doublet at about 40,000 Mr and a diffuse single band at 22,000 Mr is seen for both the reduced reference hPC and 25 mM $Ca^{2+}$ eluate. The 22,000 Mr band appearing in the hPC reference is seen to be somewhat more diffuse or heterogeneous than the similar band appearing in the 25 mM $Ca^{2+}$ eluate from the whey of transgenic mice. The sodium thiocyanate peak showed a band in excess of 180,000 Mr in the nonreduced sample and multiple bands at 50,000 Mr and 25,000 Mr in the reduced sample.

The chromatography of the WAPpC1-whey was nearly identical to the mock run using plasma-derived hPC doped into control whey. The total areas and yields of hPC in the 25 mM $Ca^{2+}$ eluates and areas of 2 M sodium thiocyanate peaks for both runs were similar and thus the binding characteristics of the 7D7B10 Mab onto transgenic hPC or plasma-derived hPC were similar. This is consistent with the similarity found between plasma-derived and transgenic hPC $Ca^{2+}$-dependent conformers as judged by ELISA assays using the 7D7B10 Mab to immunocapture from whey. The primary structure as judged by SDS-PAGE appears to be similar, with the amount of α-form and β-form heavy chain being essentially the same for plasma-derived and transgenic hPC; the transgenic having 68% α-form and 32% β-form while the plasma-derived material possessed 69% α-form and 31% β-form. The light chains were also similar in size for both reference and transgenic hPC. Previous experience with SDS-PAGE using Coomassie Blue staining of hPC has shown linearity for both chains over the range of 2–5 µg hPC applied to the gel. Thus, much of the elements of post-translational, proteolytic processing appears to have occurred properly in the mammary tissue.

The purity of these runs also demonstrates the satisfactory utility of the immunopurification procedure developed for the murine system. It is believed that the tight binding of the hPC antigen found by ELISA in the 2 M thiocyanate peak of the whey from transgenic mice (assay not done for mock run) is typical of yields found for fresh immunosorbents and not due to an aberrant hPC structure. The total background protein did not seem to condition the column and thus the interaction is thought to be specific with the 7D7B 10 Mab. Overall, this two step procedure results in a minimum purification factor of 27,000 for the hPC recovered from mouse milk. A large-scale purification process could employ a citrate or EDTA precipitation coupled with low speed centrifugation in place of the ultracentrifugation step used for mouse milk.

Both amidolytic and anti-coagulant assays were performed upon immunopurified milk from transgenic mice. Within the sensitivity of these assays, the amidolytic and anti-coagulant activity was the same as plasma-derived immunopurified protein C. For both types of assays, the specific activity was greater than 270 U/mg.

EXAMPLE 11

Highly Efficient Expression of Active Protein C in Transgenic Mammals Using a Long Mouse Whey Acid Protein Promoter Fragment and a Human Genomic Protein C Fragment (A) DNA Constructs The 5' 4.2 kb Sau3A-Kpn1 promoter fragment of the mouse whey acidic protein promoter was cloned by standard techniques. This Sau3A-KpnI WAP promoter is 4122 base-pairs in length and has the GenBank Accession No. X79437. The nucleotide sequence of the Sau3A-KpnI WAP promoter (SEQ ID NO: 1) is shown in FIG. 9. The 9.4 kb genomic fragment of human protein C beginning 21 basepairs upstream of the "A" in the protein C start codon and ending at the NheI site in the 3' end of the protein C gene also was cloned by standard techniques. The 4.2 kb promoter fragment and the 9.4 kb protein C fragment were joined using a SalI linker, as shown in FIG. 6.

(B) Production of Transgenic Animals

DNA was prepared and injected into mouse and pig embryos as described hereinabove. Animals were tested for integration of the DNA by PCR, also as described above. Stable integration of the construct was detected in both mice and pigs.

(C) Protein C in the Milk of Transgenic Mice

The mice were reared to maturity, crossed and milk was obtained from lactating females.

Figure 7A:
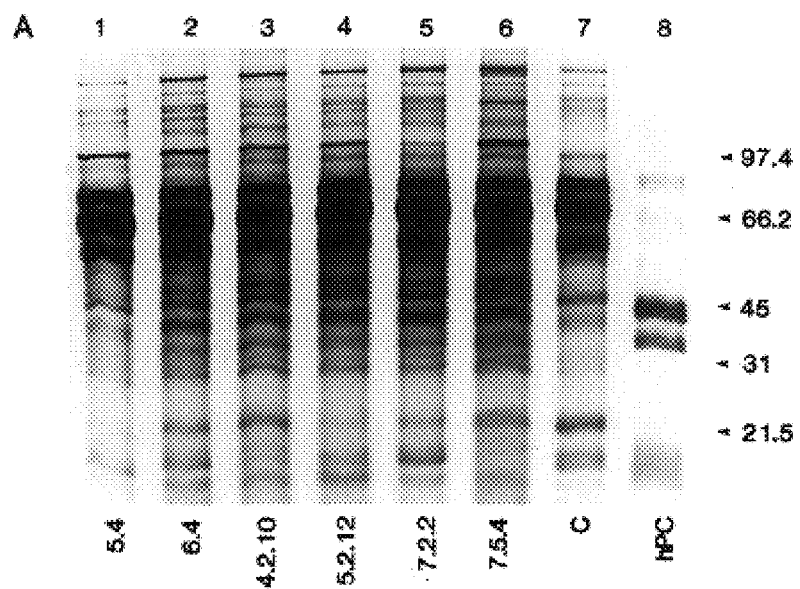
FIG. 7 is a photograph showing the results of western analyses of human protein C production in the milk of transgenic animals. Panel A shows the proteins in whey samples resolved by PAGE under reducing conditions and visualized by silver staining. Panel B shows the proteins detected by anti-human protein C antibodies in a western blot of an identical gel, visualized by chemiluminescence. Lanes were loaded with approximately 5 μg of protein. Lanes 1 through 6 contained, respectively, samples from transgenic mice 5.4, 6.4, 4.2.10, 5.2.12, 7.2.2 and 7.5.4. Lane 7 contained a sample from a non-transgenic mouse. Lane 8 contained purified human protein C. "SC"—single chain hPC, "HC"—heavy chain forms of hPC, "LC"—light chain hPC.
Figure 7B:
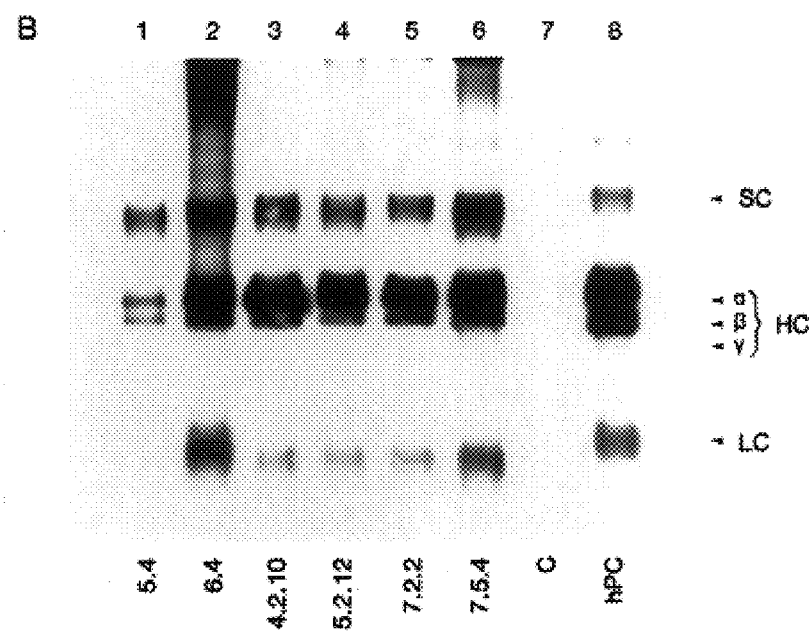

FIG. 7 depicts SDS-PAGE and western blot analysis of whey from six transgenic mice. As shown in panel A, transgenic mouse whey (lanes 1–6) and normal mouse whey (lane 7) gave rise to substantially the same silver stain pattern of bands after SDS-PAGE. As shown panel B, human protein C readily was detected in the transgenic mice whey (lanes 1–6), but not in normal mouse whey (7), when the samples were blotted onto nitrocellulose, probed with an anti-human protein C antibody, and visualized by chemiluminescence. The pattern of bands detected by the anti-human protein C antibody in the transgenic mouse whey was very similar to the pattern of bands detected in purified human protein C (lane 8).

As shown in FIG. 8, protein C activity readily could be detected in transgenic mouse whey. Panel B in the figure shows the pattern of human protein C in mouse whey samples resolved by SDS-PAGE under non-reducing conditions. Protein C was visualized by blotting onto nitrocellulose, probing the filter with an anti-human protein C antibody and detecting antibody binding by a secondary-antibody-enzyme conjugate and the chromogenic substrate 4-chloro-1-naphthol. Protein C reactive bands were substantially the same in transgenic mice (lanes 3–8) and purified human protein C (lane 1), and were absent from normal mouse whey (lane 2).

Amidolytic activity in the samples is shown in Panel A. An agarose gel overlay containing chromogenic substrate revealed enzyme activity in whey from each transgenic mouse (lanes 3–8) and in purified human protein C (lane 1), but not in normal mouse whey (lane 2). The amounts of human protein C produced by the transgenic mice in their milk also was determined. Table 5 shows the amounts of human protein C detected in the milk of six transgenic mice, as determined by 12A8 monoclonal ELISA and by sheep anti-human protein C polyclonal ELISA. The table also shows protein C amidolytic activity in whey from the same samples. The ELISAs and the amidolytic activity assay were performed as described hereinabove.

As shown in the Table 5, protein C concentrations in the transgenic mice by monoclonal ELISA ranged from approximately 0.05 mg/ml to approximately 1.69 mg/ml. The concentration of protein C in the milk of these mice was at least 40 fold more than the concentration of protein C observed in other transgenic mice, such as those noted in Table 2A, as set forth hereinabove.

Concentrations measured by polyclonal ELISA ranged from 0.14 to 4 mg/ml, exceeding even more dramatically the concentrations attained with the 2.4 kb 5' WAP promoter, the highest of which, as set forth in Table 2A, was 0.0041 mg/ml.

In addition, whey samples from the transgenic mice were assayed for amidolytic activity and the results were compared with amidolytic activity of protein C in plasma. Amidolytic activity in the samples is shown in Table 5, expressed as the per cent of protein C activity in plasma. The concentration of protein C in the whey samples was adjusted to equal the concentration in the normal plasma control.

The high concentration of protein C allowed the amidolytic activity to be assayed directly in whey. This contrasted sharply with the necessity to use a capture method to concentrate protein C prior to amidolytic activity of whey samples from mice transgenic for the 2.4 kb WAP promoter fragment.

The amidolytic activity of protein C in the whey sample was also compared with the activity of purified human protein C diluted in whey. At comparable concentrations of protein C, amidolytic activity in transgenic mouse whey was nearly the same as that of human protein C.

TABLE 5

Detection of human protein C in the milk of transgenic mice having the 5' 4.2 kb WAP-promoter-9.4 kb human genomic protein C construct stably integrated in their genomes

| MOUSE NUMBER | TRANSGENE COPY NUMBER | PC ANTIGEN BY 12A8-MAB ELISA (mg/ml) | PC ANTIGEN BY POLY-CLONAL ELISA (mg/ml) | AMIDOLYTIC ACTIVITY IN WHEY (% N-PLASMA) |
|---|---|---|---|---|
| 5.4 | 14 | 0.05 ± −0.01 | 0.14 ± −0.01 | N.D. |
| 6.4 | 10 | 1.00 ± −0.03 | 2.94 ± −0.09 | 56.2 |
| 4.2.10 | 10 | 1.69 ± −0.09 | 3.98 ± −0.09 | 54.8 |
| 5.2.12 | 20 | 0.96 ± −0.09 | 2.50 ± −0.10 | 54.9 |
| 7.2.2 | 2 | 0.33 ± −0.03 | 0.89 ± −0.14 | N.D. |
| 7.5.4 | 30 | 0.96 ± −0.04 | 1.99 ± −0.33 | 18.8 |

Finally, some of the transgenic mice were sacrificed and examined to determine the tissue specificity of expression of human protein C. RNA blots and immuno in situ histological examination showed that at least 99% of the protein C expression occurred in the mammary glands in these animals. These results contrast with the results achieved using whey acidic protein promoter constructs that contained only the 2.4 kb promoter fragment. Constructs using this promoter to drive protein expression in transgenic mice engendered expression that differed from the normal pattern of whey acidic protein expression during development and in adult tissues. In fact, this was true for the whey acidic protein itself. Thus, in addition to providing high levels of expression of a protein, the 4.2 kb 5' WAP promoter fragment also provides greater tissue specificity of expression in the adult mouse.

(D) Purification of Protein C from Transgenic Mouse Whey

Human protein C was partially purified from transgenic mouse whey by immunoaffmity chromatography using the 12A8 monoclonal antibody immobilized on a Sepharose support. Bound protein C was eluted in 0.1 M glycine, 0.02 M histidine, 0.15 M NaCl pH 10. Transgenic protein C purified in this manner revealed essentially the same banding pattern upon SDS-PAGE as a standard preparation of purified human protein C.

EXAMPLE 12

Preparation of DNA Constructs Containing a Mouse Long Whey Acid Protein Promoter Fragment and a Factor IX DNA for Expression in Transgenic Animals Generally, the entire murine WAP gene was cloned by standard methods, as described above. Generally, the entire murine WAP gene including 2.5 kb of 5' untranslated sequence and 3' untranslated regions was cloned by standard methods. See Campbell et al., *Nucleic Acids Res*. 12:8685 (1984). A cDNA fragment encoding human Factor IX was obtained and the 3' untranslated region was deleted. Using standard methods, an expression vector was constructed that contained a mouse WAP promoter, isolated as a 2.6 kb EcoRI-KpnI fragment immediately 5' to the WAP signal sequence, the human Factor IX cDNA sequence lacking a 3' untranslated region, and a 1.6 kb fragment of the 3' untranslated region of the WAP gene. A second expression vector contained a 7.2 kb mouse WAP gene (EcoRI-EcoRI) fragment. Expression vectors were amplified by bacterial transformation and purified from bacterial cultures using standard methods. Routine recombinant DNA techniques can be found, for example, in Sambrook et al., MOLECULAR CLONING, A LABORATORY MANUAL, Vol. 1–3 (Cold Spring Harbor Press 1989). More specifically, a chimeric Factor IX construct was prepared, as follows:

(A) Preparation of a Chimeric Factor IX Construct

1. Production of pWAP4 "Cassette Vector"

Regulatory 5' and 3' flanking sequences of the mouse WAP gene were used for mammary specific expression. Specifically, a cassette vector containing a mouse WAP promoter, defined as a 2.6. kb EcoRI-KpnI fragment immediately 5' to the WAP signal sequence and a 1.5 kb fragment of the 3' untranslated region of the WAP gene was prepared. These regulatory sequences do not include coding and intragenic untranslated sequences (introns) of the WAP gene.

Figure 10A:
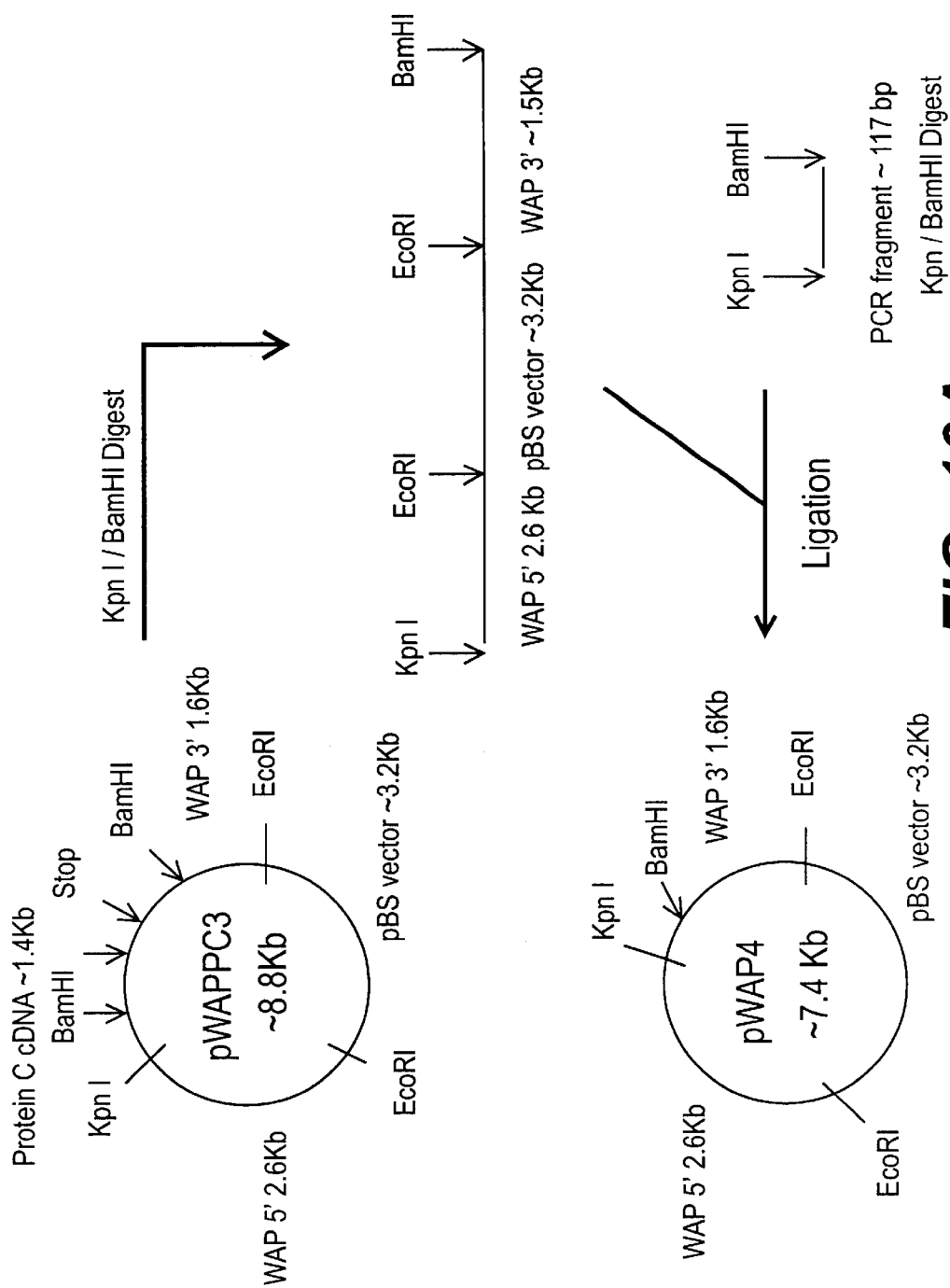
FIGS. 10A–10D schematically depict the construction of a chimeric Factor IX (FIX) construct containing the short WAP promoter. Specifically.

The vector designated pWAP4 was derived from pWAPPC3 (C. Russell, dissertation "Improvement of Expression of Recombinant Human Protein C in the Milk of Transgenic Mammal Using a Novel Transgenic Construct," Virginia Technology Institute, Blacksburg, Va. (December 1993)) and was developed as follows: Using WAPPC3 as a template, PCR primers WAP3'S2 (which contains a 5'KpnI site and is homologous to endogenous WAP right after the stop signal) and WAP3'A1, as shown in Table 6, below, were used to produce a segment with KpnII and BamHI sites on either end. This segment was digested with KpnI/BamHI and ligated with the vector containing the fragment from KpnI/BamHI digested pWAPPC3. The ligation mixture was used to transform *E. Coli* DH5α cells by electroporation with resultant colonies grown on LB ampicillin plates. Picked colonies were grown up in TB ampicillin broth, plasmids isolated and cut with KpnI, BamHI or both and subjected to gel electrophoresis. Sequencing was performed using WAP3'A1 primer and judged as being correct. See FIG. 10A.

TABLE 6

| Primer Sequences | |
|---|---|
| SEQ ID NO: 2 humFIX5'KpnI | 5'gcta\ggtacc\atgcagcgcg |
| SEQ ID NO: 3 humFIX3'KpnI | 5'gtca\ggtacc\ttaagtgagct |
| SEQ ID NO: 4 FIXS1 | 5'ggataacatcactcaaagcac |
| SEQ ID NO:5 WAP3'A1 | 5'tagcagcagattgaaagcattatg |
| SEQ ID NO: 6 FIXA1 | 5'gtgaactttgtagatc |

2. Production of Modified (Kpn I) FIX cDNA

The FIX cDNA (containing Kpn I sites located immediately before the start sequence and after the stop sequence) was generated as a PCR fragment. Fragment production protocol is as follows: 100 μl total volume containing 200 μM dNTP's, 0.5 μM of each primer (humFIX5'KpnI and humFIX3'KpnI, as shown in Table 6), 2.5 units Pfu polymerase and 30 ng of plasmid template (pMCDSFIX obtained from Prof. Darryl Stafford, Department of Biology, University of North Carolina, Chapel Hill, N.C., USA), reaction mixture was subjected to 30 cycles of denaturation at 95° C. for 20 sec, annealing at 50° C. for 1 min and elongation at 75° C. for 5 min 45 sec. After cycling, the reaction mixture was subjected to blunting with T4 DNA polymerase for 10 min, EDTA concentration brought up to 25 mM, heated to 65° C. for 15 min, and extracted with Phenol: Chloroform (1:1), precipitated with equal volumes of 95% ethanol, aspirated, and suspended in $H_2O$.

3. Ligation, Transformation and Sequencing

Figure 10B:
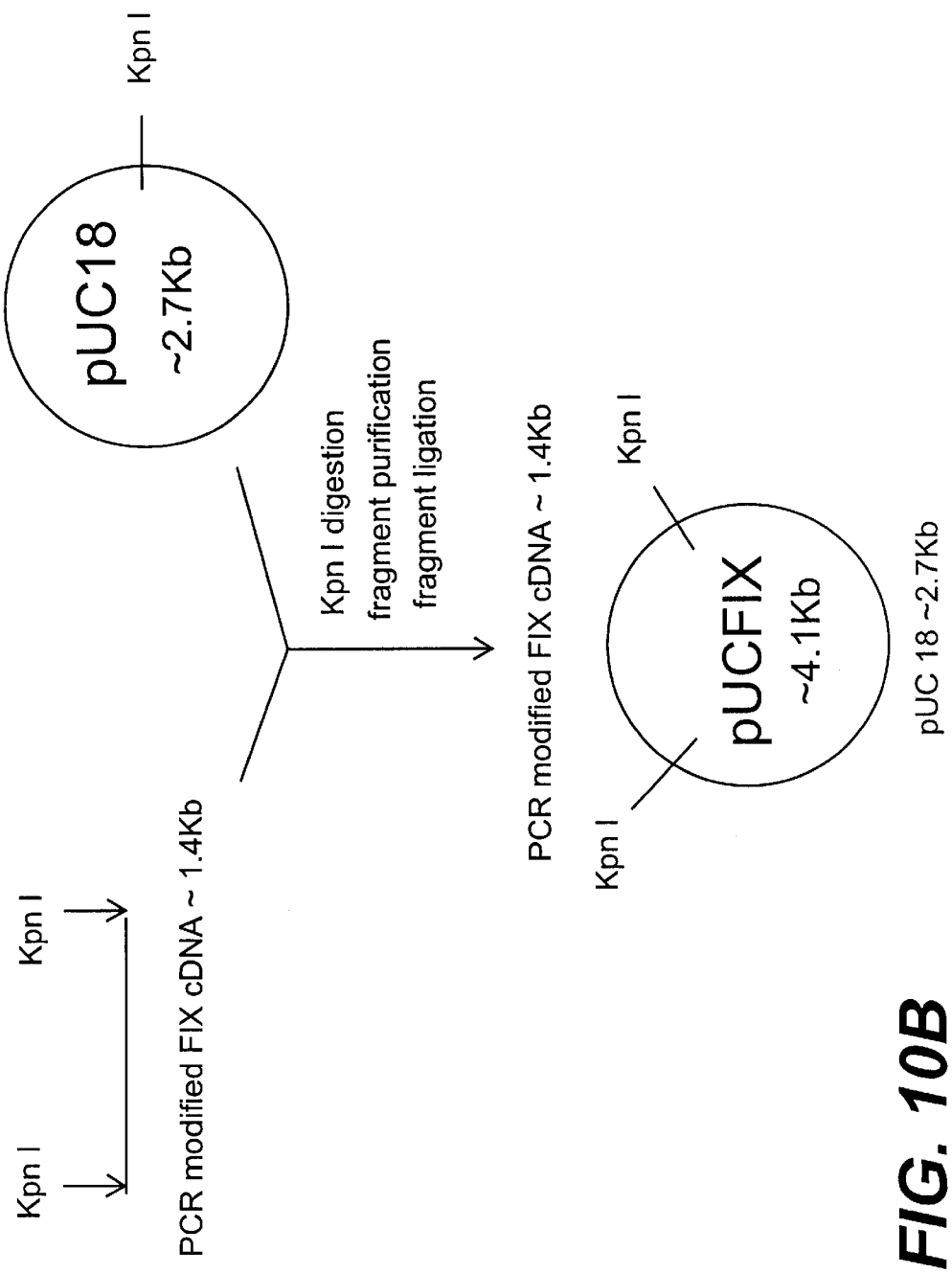

As is shown in FIG. 10B, the plasmid designated pUCFIX containing the modified (Kpn I ends) FIX cDNA was produced by digestion of both pUC18 and the modified cDNA with Kpn I (per manufacturers instructions, Stratagene, La Jolla, Calif.) purification of digestion products by $CHCl_3$: Phenol (1:1) extraction, precipitation with equal volumes of 95% ethanol, aspiration and suspension in $H_2O$. Ligation of plasmid and cDNA was per manufacturers instructions (Stratagene) using 125 ng of Kpn I digested pUC18 and 125 ng of Kpn I digested modified cDNA. *E. coli* JM109 was transformed by electroportation using ligation mixture and plated on LB ampicillin plates. Selected colonies were grown up in TB ampicillin broth. Plasmid preparations from these colonies were analyzed by restriction enzyme digestion (Kpn I) and gel electrophoresis. The entire sense strand of the cDNA was sequenced and found to be correct as compared with FIXA sequences located in GenBank.

4. Introduction of FIX cDNA into pWAP4 "cassette vector" to produce pWAPFIX

Figure 10C:
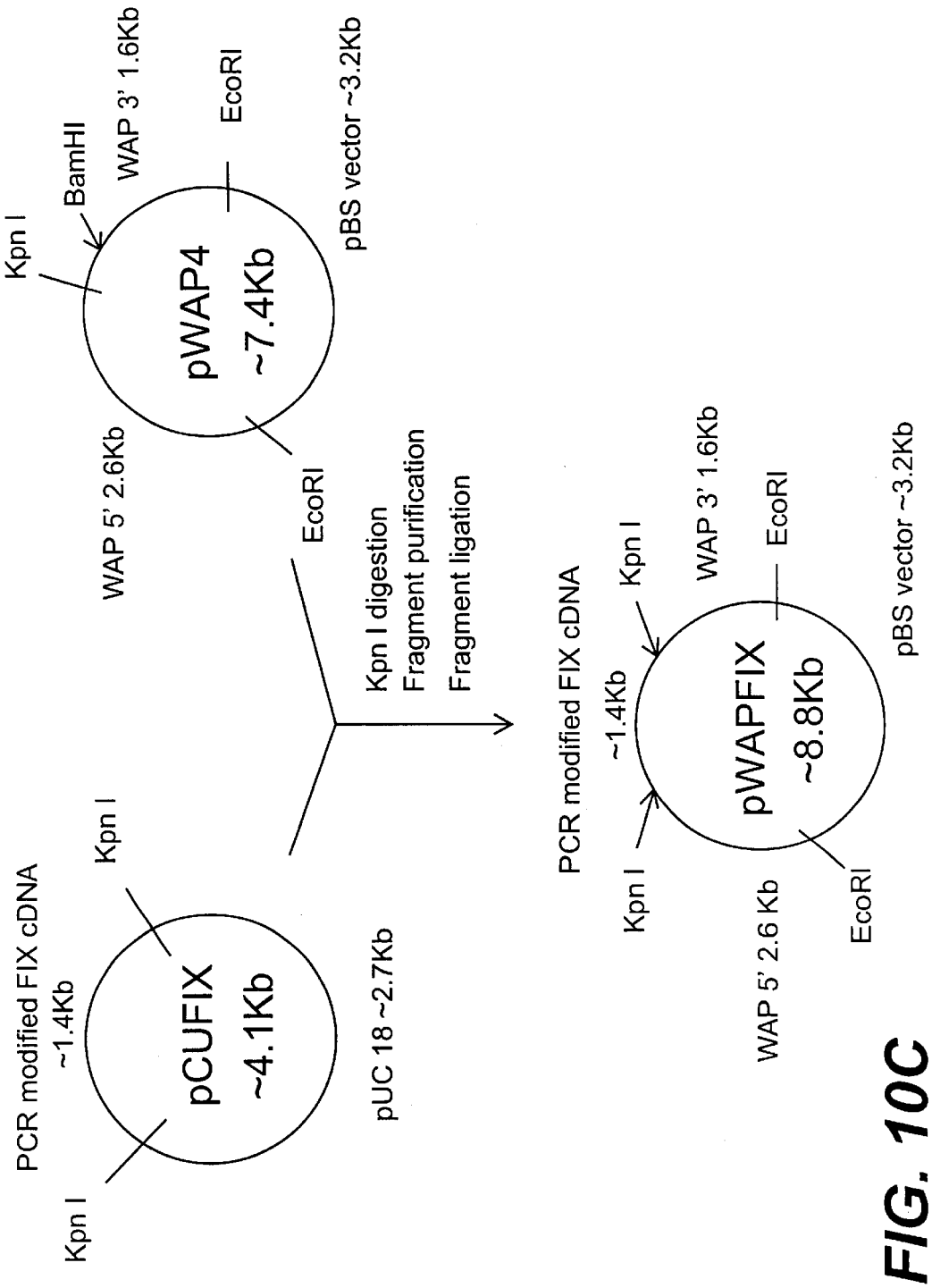

As shown in FIG. 10C, both pWAP4 and pUCFIX were digested with Kpn I in separate reactions, subjected to gel electrophoresis and the appropriate plasmid fragments removed from the gel and ligated. *E. coli* JM109 was transformed by electroportation using ligation mixture and plated on LB ampicillin plates. Selected colonies were grown up in TB ampicillin broth. Plasmid preparations from these colonies were analyzed by restriction enzyme digestion (Kpn I) then gel electrophoresis. Clones positive for the insert were subjected to PCR analysis using primers FIXS1 and WAP3'A1 to determine the correct orientation of the insert.

Figure 10D:
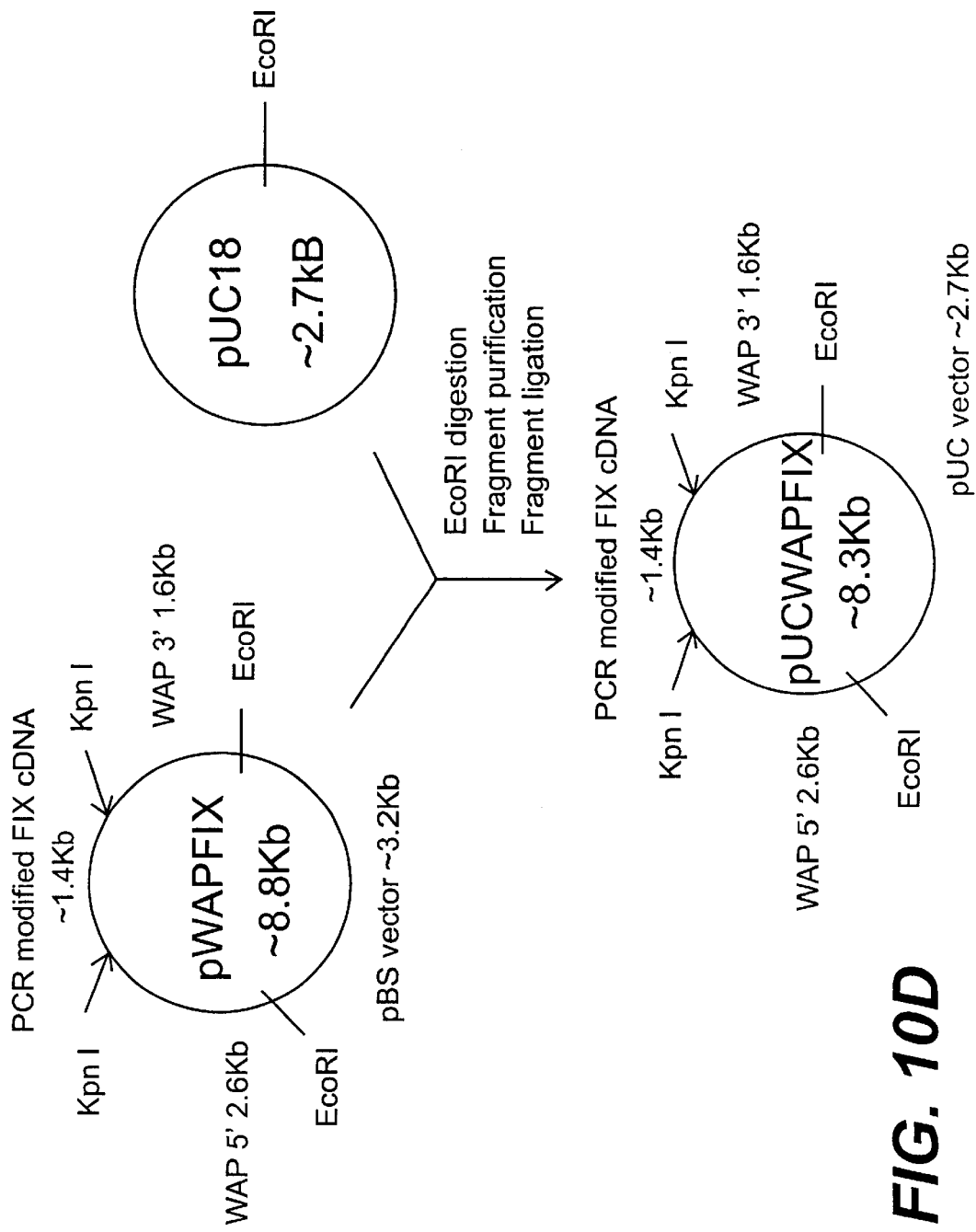

As shown in FIG. 10D, the insert containing WAP promoter, cDNA and 3'WAP UTR was released from pWAP-FIX by EcoRI digestion, subjected to gel electrophoresis, removed from the gel and purified. This fragment was ligated with Kpn I digested pUC18 and the reaction mixture used to transform *E.coli* JM109 by electroportation. After electroportation, cells were plated on LB ampicillin plates with picked colonies grown in TB ampicillin broth. Plasmids from picked colonies were purified and subjected to EcoRI enzyme digestion and electrophoresis. After insert confirmation, large scale purification was undertaken, according to methods well known to the skilled artisan.

(B) Production of Constructs Containing the Long WAP Promoter

Specifically, a cassette vector containing a mouse long WAP promoter, defined as a 4.1 kb NotI-Kpn1 fragment immediately 5' to the WAP signal sequence and a 1.6 kb fragment of the 3' untranslated region of the WAPgene was prepared. These regulatory sequences do not include coding and intragenic untranslated sequences (introns) of the WAP gene.

The vector designated pUCWAP6 was derived from genetic elements from the following plasmids as starting material: pUC18, pWAP4 and p227.6, which were provided by the American Red Cross. The development of pUCWAP6 is as follows: The pUC18 vector was cut with the enzymes EcoRI and Hind III to remove the multiple cloning site of the vector, blunted with exonuclease and ligated with NotI linkers. The linearized plasmid was then cut with NotI and ligated. Ligation mixture was used to transform *E. coli* DH5α cells on LB ampicillin plates, picked colonies were grown in TB ampicillin broth, plasmids were isolated and cut with NotI then subjected to gel electrophoresis. A plasmid was judged to be correct and designated as pUC-NotI (See FIG. 11A). The vector pWAP4 as described above and as described in U.S. Ser. Nos. 08/198,068 and 08/443,184, was cut with EcoRI and the fragment containing the WAP 5' 2.6 kbp and 3' genetic elements were separated by gel electrophoresis and purified. The ends of the fragment were modified by blunting with exonuclease and NotI linkers were ligated on. The fragment was cut with NotI and ligated into the NotI restriction site of pUCNotI then used to transform *E. coli* DH5α cells on ampicllin plates picked colonies were grown in TB ampicillin broth. Isolated plasmid was verified to be correct by NotI digestion with the plasmid being designated pUCWAP5. The pUC WAP5 plasmid was subjected to KpnI digestion and a partial NotI digestion producing a fragment that contained the pUCNotI vector sequence flanked by the mWAP 3'UTR (See FIG. 11B). This fragment was ligated with the 4.1 kb 5' WAP promoter produced from digestion of p227.6 with NotI, KpnI and Hind III. The ligation mixture was then used to transform *E. coli* JM109 cells that were grown on LB ampicillin plates picked colonies were grown in TB ampicillin broth, plasmids isolated were cut with NotI, and NotI/KpnI and judged to be correct. The plasmid was then designated pUCWAP6 (See FIG. 11C).

Figure 12:
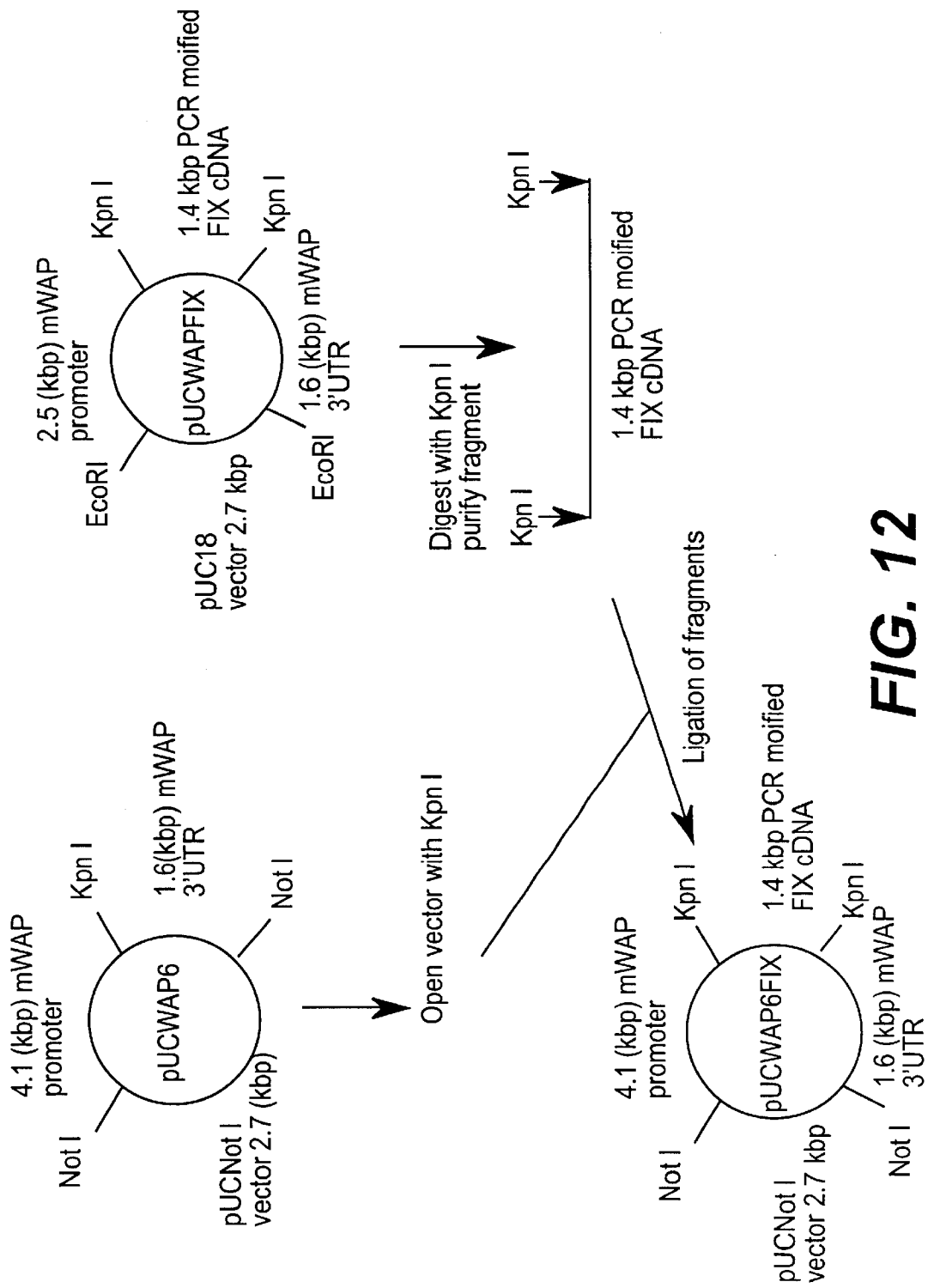
FIG. 12 shows the production of pUCWAP6FIX.

As shown in FIG. 12, the plasmid pUCWAP6FIX was produced by digestion of pUCWAPFIX with KpnI and isolating the FIX cDNA by gel electrophoresis. This fragment was inserted into the KpnI site of pUCWAP6 after KpnI digestion and both fragments were then subjected to ligation. The ligation mixture was then used to transform *E. coli* JM109 cells that were then plated on LB ampicillin plates. Picked colonics were grown in TB ampicillin broth and plasmids were isolated. Isolated plasmids were digested with NsiI to verify orientation of the cDNA insert. Plasmids that contained the insert in the correct orientation were designated pUCWAP6FIX. After inert confirmation, large scale purification was undertaken, according to methods well known to the skilled artisan. DNA was prepared for microinjection and injected into animals as described above and as is known by persons skilled in the art. Analysis of Factor IX DNA derived from the tissue of the transgenic animals and the analysis of the Factor IX produced in the transgenic animals are performed by methods well known to persons skilled in the art and as described in PCT/US98/02638, a continuation-in-part of provisional U.S. Pat. No. 60/037,145, which are both incorporated in their entirety by reference. Factor IX was expressed in transgenic animals made from the constructs described in the present invention.

EXAMPLE 13

Construction of Expression Vectors Containing a Long Mouse Whey Acid Protein Promoter Fragment and Fibrinogen (FIB) DNA for Expression in Transgenic Animals (A) Construction of Cassette Vectors FIB subunit chain DNAs, tissue-specific promoters, and secretion signal sequences were obtained from sources described above. FIB subunit chain cDNAs were cloned into a modified pUC 18 vector, and grown up in *E. coli* JM109. A pUC18 vector (GIBCO-BRL, Gaithersburg, Md.) was digested with HindIII+ EcoRi restriction endonucleases, blunted with T4 DNA polymerase in the presence of 100 mM dNTPs, and a Not I linker was ligated into the former HindIII-EcoRI multiple cloning site. This modified pUC fragment was additionally digested with Not I+ enzyme to remove extra (multiple copies) NotI linker sequences arising from ligation, and then religated and grown up in *E. coli* JM 109. This procedure modified the pUC18 vector by removing the entire multiple cloning region of pUC18 (including the Kpn I site) and replacing it with a Not I restriction site. The new vector was designated pUCNot1 +.

Figure 11A:
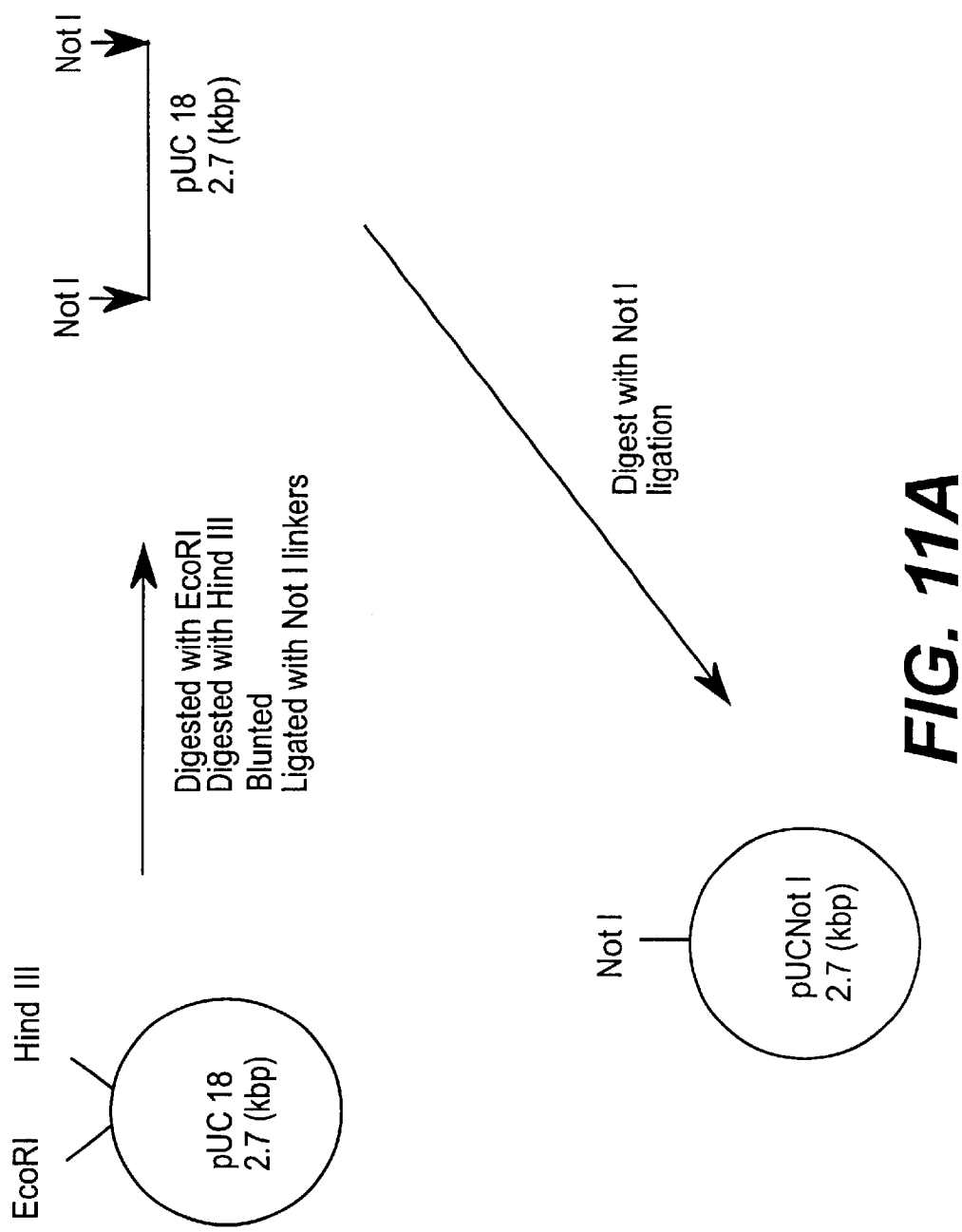
FIGS. 11A–11C show the production of the pUCWAP6 "cassette vector." Specifically.
Figure 11B:
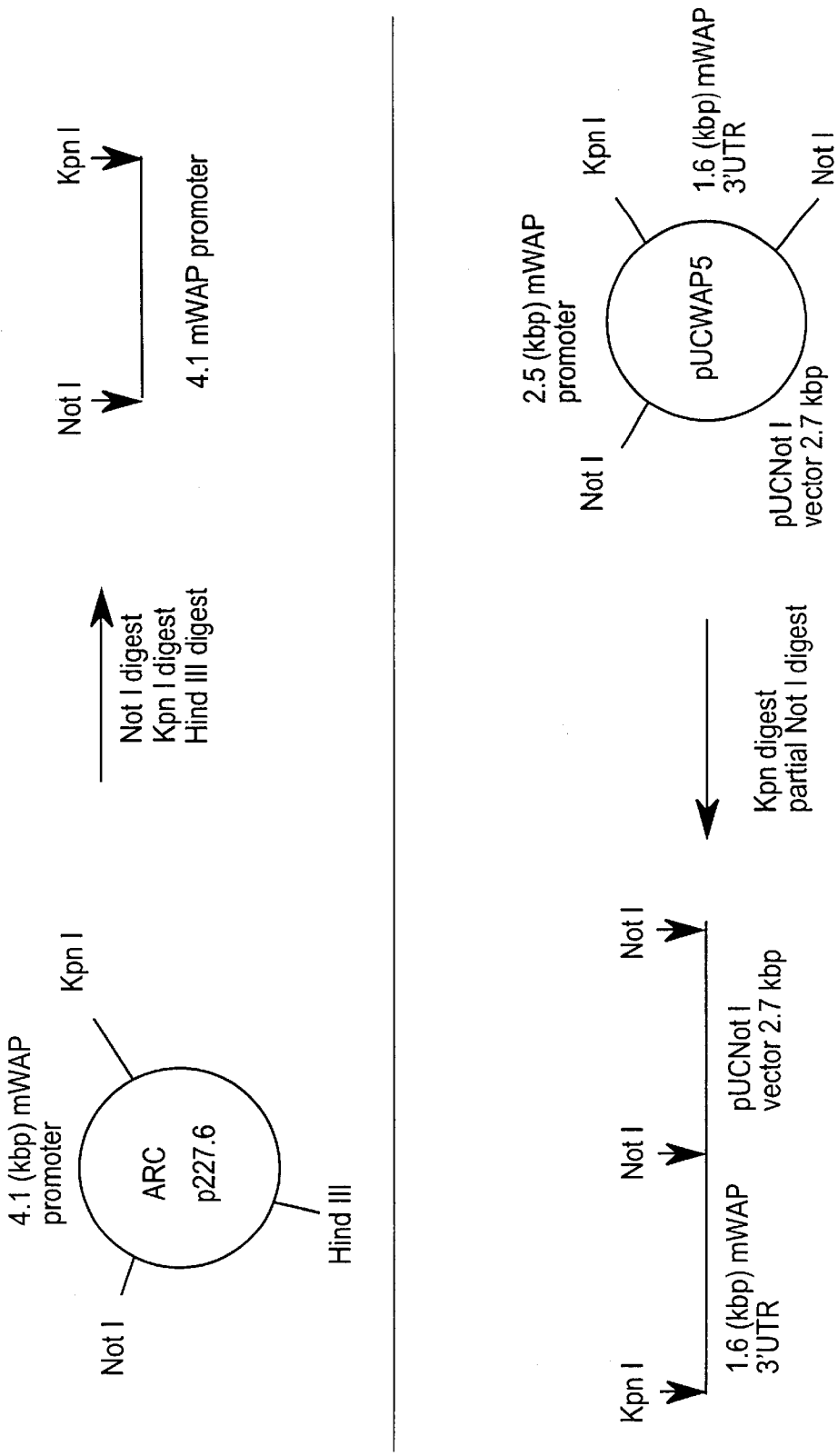
Figure 13:
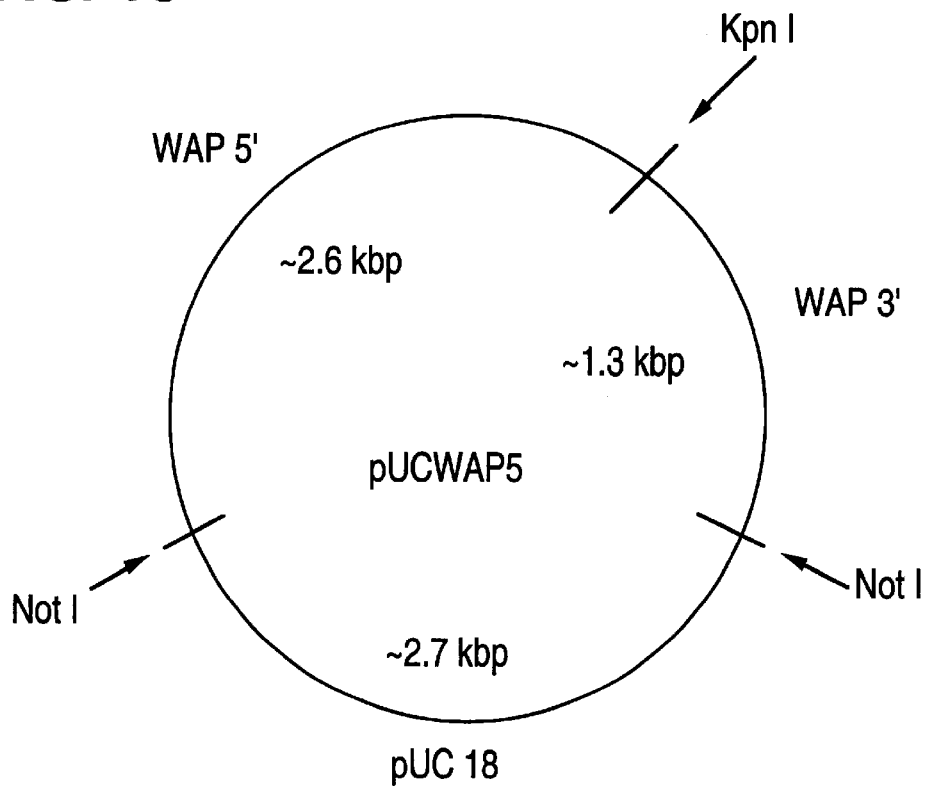
FIG. 13 shows the pUCWAP5 cassette vector containing the WAP fragment of pUCWAP4 with added Not I linkers.

A pUC vector containing ~2.6 kbp of WAP 5' promoter region, ~1.3 kbp of WAP 3' UTR and flanking 3', but no WAP coding or intronic regions was constructed (designated cassette vector pUCWAP4, as described in Example 12 and as shown in FIG. 11A). The WAP fragment contained within the WAP4 vector contains a ~2.6 kbp WAP promoter 5' region beginning at EcoRI#1 and ending at the translational start site of WAP which is immediately downstream of the unique Kpn I endonuclease restriction site. To this KpnI site was ligated a fragment of ~1.3 kbp of WAP UTR and flanking 3' sequence. This WAP 3' DNA included the region from immediately downstream of the WAP stop codon down to the EcoRI#2 site. The WAP fragment contained in WAP4 was excised from the pUC vector using EcoRI, and then blunted, and NotI linkers were added, further trimmed by NotI digestion, and ligated into the pUCNotI+ plasmid which had been linearized with NotI restriction endonuclease. The resulting plasmid was designated pUCWAP5 (see FIG. 13).

(2) Amplification by PCR of Fibrinogen Subunit Chain cDNAs

The DNA sequences encoding the Aα, Bβ, and γ chains for human fibrinogen (hFIB) are known and disclosed. Fibrinogen cDNA sequences encoding the human fibrinogen Aα, Bβ, and γ chains are known and published. See, e.g. Rixon et al., *Biochemistry* 22, 3237–3244 (1983), Chung et al., *Biocehmistry* 22, 3244–3250 (1983) and Chung et al., *Biocehmistry* 22, 3250–3256 (1983). The genomic DNA sequences encoding the human fibrinogen Aα, Bβ, and γ chains are known and published. See, e.g. Chung et al., *Adv. Exp. Med. Biol.* 281, 39–48 (1990). Each of the cDNAs for Aα, Bβ, and γ chains for human fibrinogen were individually modified and amplified by polymerase chain reaction (PCR) to create KpnI endonuclease restriction sites on their 5' and 3' ends. The 5' KpnI site was engineered by PCR using the primers [containing the 6 base sequence (GGTACC shown underlined in Table 7)] that immediately flanks the ATG start codon in the cDNAs of Aα, Bβ, and γ chains for hFIB. After amplification, the ends of the extension using PCR products were blunted by T4-polymerase (in the presence of deoxynucleosidetriphosphates to inhibit processive exonuclease activity. In a similar fashion, a KpnI site was engineered by site modification into the 6 base sequence GGTACC shown underlined in Table 7 immediately flanking the stop sequence in the 3' UTR of each cDNA for Aα, Bβ, and γ chains for hFIB. The complement of the stop sequences is shown in bold in the 3' primers in Table 7.

TABLE 7

Oligonucleotides for Amplifying FIB Subunit Chain cDNA

Seq. ID No: 7
Aα 5' GCT<u>AGGTACC</u>ATGTTTTCCATGAGGATCGT

TABLE 7-continued

Oligonucleotides for Amplifying FIB Subunit Chain cDNA

Seq. ID No: 8
Aα 3' CAGTGGTACCCTAGACAGGGCGAGATTTAG

Seq. ID No: 9
Bβ 5' GCTAGGTACCATGAAAAGAATGGTTTCGTG

Seq. ID No: 10
Bβ 3' CAGTGGTACCCTATTGCTGTGGGAAGAAGG

Seq. ID No: 11
γ5' GCTAGGTACCATGAGTTGGTCCTTGCACCC

Seq. ID No: 12
Gγ3' CAGTGGTACCTTAAACGTCTCCAGCCTGTT

Figure 14:
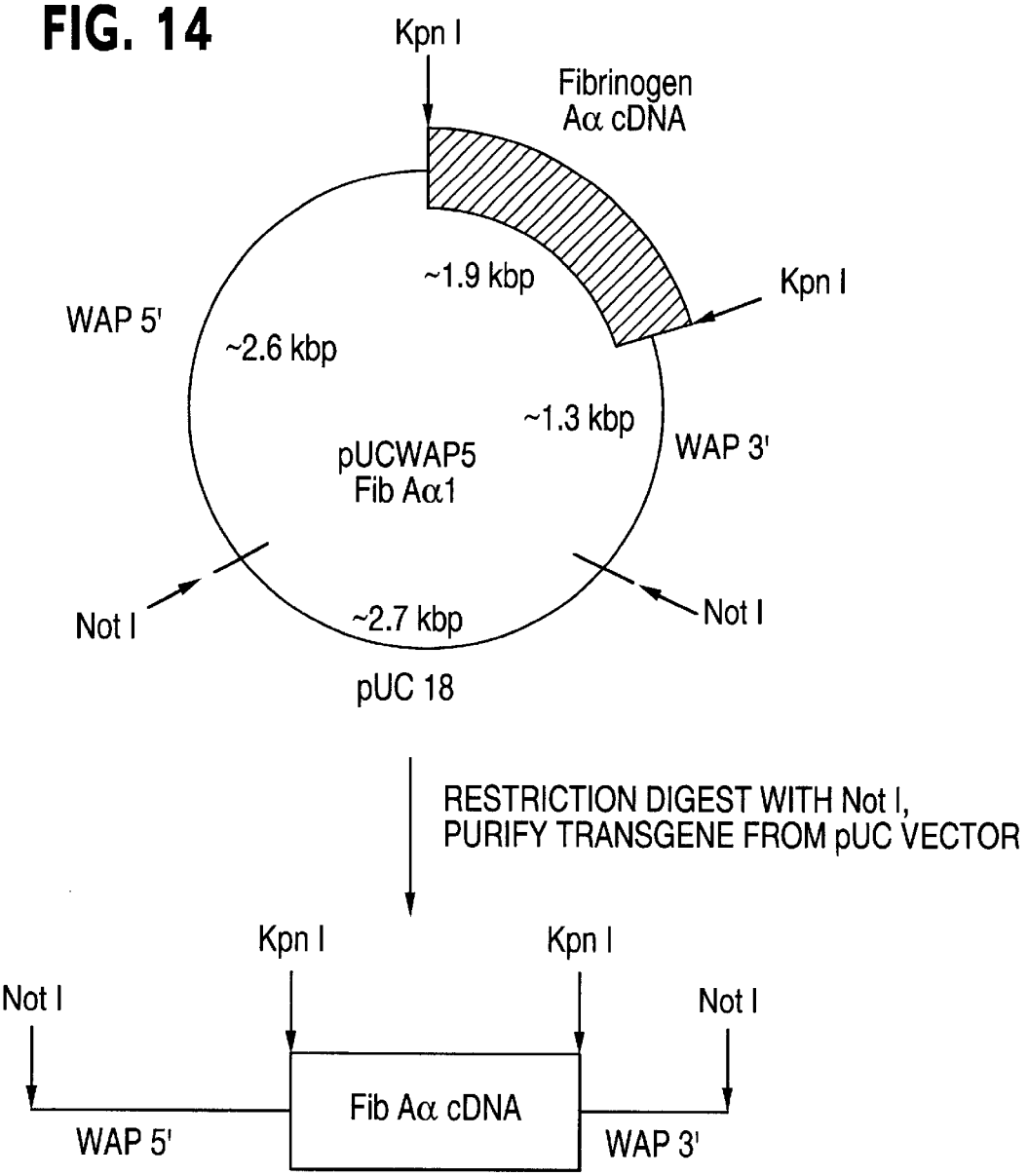
FIG. 14 shows the pUCWAP5 incorporating a polynucleotide encoding the FIB Aα 1 chain.
Figure 15:
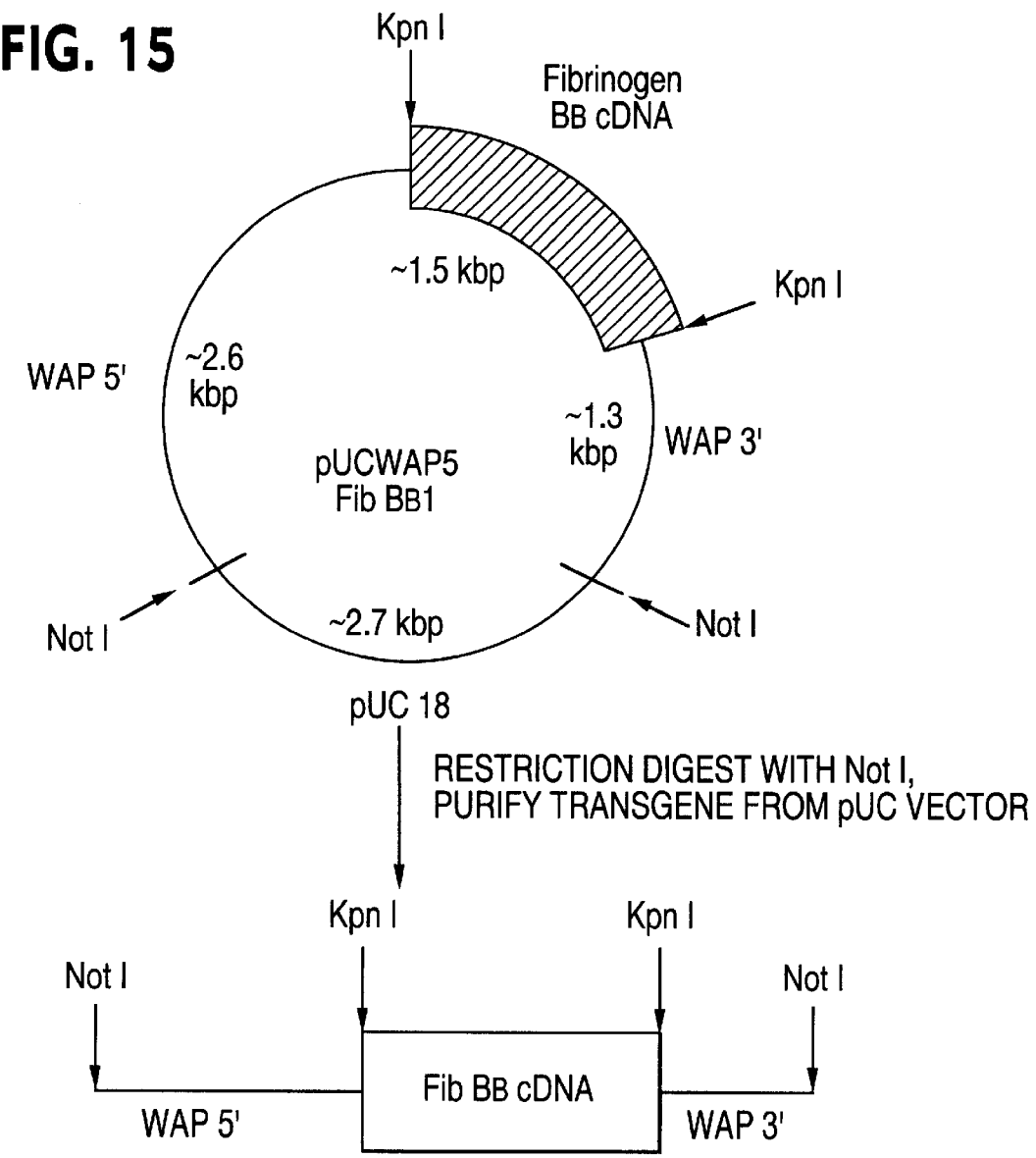
FIG. 15 shows the pUCWAP5 incorporating a polynucleotide encoding the FIB Bβ 1 chain.

GGTACC = KpnI site
ATG = start codon
CTA and TTA = stop codon (C) Construction of pUC Plasmids Containing Fibrinogen Subunit Chain cDNA The blunted PCR products of the cDNAs for the Bβ and γ chains of hFIB were digested with KpnI restriction endonuclease. In the case of the Aα chain, the PCR product was blunt-end cloned into pUCNotI+ (which had been digested with NotI and blunted with T4 Polymerase) prior to partial KpnI digestion. This intermediate cloning and partial digestion step was necessary to generate intact coding fragment due to the presence of an internal KpnI site within the Aα chain cDNA. The intact Aα chain cDNA fragment was selected by gel electrophoresis, and cloned into the KpnI site at the junction between the WAP 5' promoter and WAP 3' UTR/flanking sequences within the pUCWAP5 plasmid. The KpnI-digested PCR products from Bβ and Gγ chains for human fibrinogen were each directly cloned into a pUCWAP5 plasmid at the KpnI site. Separate electroporation transformation reactions were done on *E. coli* using each of the three pUCWAP5/fibrinogen cDNA preparations, and colonies were picked and grown up in TB ampicillin broth. Plasmid preparations from these colonies were analyzed by restriction enzyme digestion and gel electrophoresis. The correct size and orientations were selected and one clone for each WAP-fibrinogen cDNA construct was sequenced at the WAP promoter 5':fibrinogen cDNA and fibrinogen cDNA:WAP 3' UTR and flanking junctions. Schematics summarizing the construction of the WAP-Aα (about 5.8 kbp), -Bβ (about 5.4 kbp), and -γ (about 5.2 kbp) cDNA plasmid and linearized transgenes for human fibrinogen are given in FIGS. 14, 15, and 16, respectively.

Figure 11C:
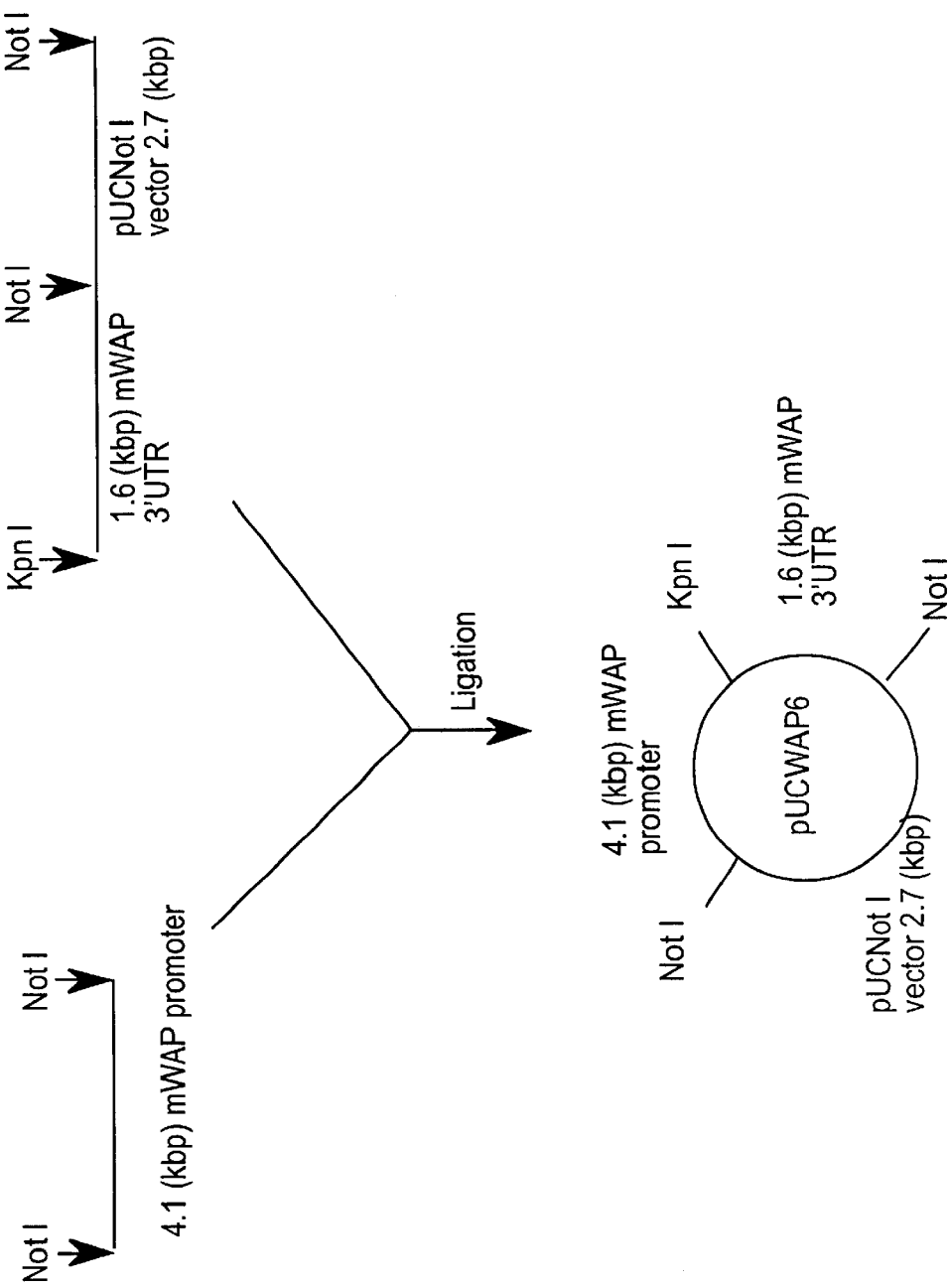

Each of the pUCWAP5-Aα, pUCWAP5-Bβ and pUCWAP5-γ are digested with KpnI and the DNA fragments encoding the Aα, Bβ, and γ chains were isolated by gel electrophoresis. The plasmid pUCWAP6 as shown in FIG. 11C was digested with KpnI as shown in FIG. 12 for the preparation of Factor IX long WAP constructs. Each of the fragments encoding the Aα, Bβ, and γ chains was inserted into the KpnI site of pUCWAP6 after KpnI digestion and both fragments were then subjected to ligation. The ligation mixture was then used to transform *E. coli* JM109 cells that were then plated on LB ampicillin plates. Picked colonies were grown in TB ampicillin broth and plasmids were isolated. Isolated plasmids were digested with NsiI to verify orientation of the cDNA insert. Plasmids that contained the insert in the correct orientation were designated pUCWAP6-Aα, -Bβ and γ, respectively. After inert confirmation, large scale purification was undertaken, according to methods well known to the skilled artisan. DNA was prepared for microinjection and injected into animals as described above and as is known by persons skilled in the art. Analysis of hFIB DNA derived from the tissue of the transgenic animals and the analysis of the hFIB produced in the transgenic animals are performed by methods well known to persons skilled in the art and as described in U.S. Ser. Nos. 08/443,184 and 08/198,068, which are both incorporated in their entirety by reference. The expression of fibrinogen in transgenic animals made from some of the constructs described in the present application is disclosed in Butler et al., *Thrombosis and Haemostasis*, 78(1) 537–542 (1997).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What we claim is:

1. An isolated DNA sequence which regulates the expression of a heterologous gene, wherein the DNA sequence comprises a mouse whey acidic protein promoter having a length of greater than about the length of the EcoRI-KpnI promoter of the mouse whey acidic protein gene.

2. An isolated DNA sequence according to claim 1, wherein the DNA sequence comprises a mouse whey acidic protein promoter having a length of greater than about the length of the EcoRI-KpnI promoter of the mouse whey acidic protein gene to less than about the length of the Sau3A-KpnI promoter of the mouse whey acidic protein gene.

3. An isolated DNA sequence according to claim 2, wherein the DNA sequence has functionally equivalent promoter activity to the mouse whey acidic protein 4.2 kb Sau3A-KpnI promoter.

4. An isolated DNA sequence according to claim 1 comprising at least the approximately 4.2 kb Sau3A-KpnI promoter.

5. An isolated DNA sequence according to claim 1 comprising at least the NotI-KpnI promoter of the mouse whey acidic protein gene.

6. An isolated DNA sequence according to claim 1, operably linked to a DNA sequence encoding a heterologous polypeptide and a 3'-untranslated region from a mammary gland-specific gene or 3'-untranslated region active in a mammary gland.

7. An isolated DNA sequence according to claim 6, wherein said 3'-untranslated region is the 1.6 kb fragment of the mouse whey acidic protein gene.

8. A transgenic non-human mammal containing a DNA sequence stably integrated in its genome, wherein said DNA sequence comprises a mouse whey acidic protein promoter having a length of greater than about the length of the EcoRI-KpnI promoter of the mouse whey acidic protein gene, operably linked to a DNA sequence encoding a heterologous polypeptide, whereby said polypeptide is expressed specifically in mammary cells of said transgenic mammal and said polypeptide comprises a signal peptide, said signal peptide being effective in directing the secretion of said polypeptide into the milk of said mammal.

9. The transgenic non-human mammal of claim 8, wherein said transgenic non-human mammal is selected from the group consisting of mice, rats, rabbits, pigs, sheep, goats and cows.

10. The transgenic non-human mammal of claim 9, wherein said mammal is a sheep.

11. The transgenic non-human mammal of claim 9, wherein said mammal is a goat.

12. The transgenic non-human mammal of claim 9, wherein said mammal is a cow.

13. The transgenic non-human mammal of claim 9, wherein said mammal is a pig.

14. The transgenic non-human mammal of claim 8, wherein said heterologous polypeptide is a blood protein.

15. The transgenic non-human mammal of claim 14, wherein said blood protein is protein C, Factor IX, fibrinogen or Factor VIII.

16. The transgenic non-human mammal of claim 8, wherein said heterologous polypeptide is protein C, wherein the activated form of said secreted protein C has an enzymatic activity of at least 50% as plasma-derived protein C, and wherein said transgenic mammal is selected from the group consisting of mice, rats, rabbits, pigs, sheep, goats and cows.

17. The transgenic non-human mammal of claim 16, wherein said DNA sequence encoding the heterologous polypeptide comprises the human protein C gene from 21 basepairs upstream of the protein C start codon to the NheI site in the 3' end of the protein C gene.

18. The transgenic non-human mammal of claim 8, wherein said DNA sequence encoding said heterologous polypeptide further comprises regulatory elements located in the non-coding regions of the heterologous protein gene, wherein said regulatory elements are at least one of the AUG start codon, donor and acceptor splice signals, the secretion peptide, translation termination signal, transcription termination signal, and polyadenylation signal.

19. A process for the production of a heterologous polypeptide in the milk of a transgenic non-human mammal, comprising the steps of:

(A) providing a transgenic non-human mammal whose genome comprises a stably integrated DNA sequence comprising a mouse whey acidic promoter having a length of greater than about the length of the EcoRI-KpnI promoter of the mouse whey acidic protein gene, operably linked to a DNA sequence encoding a heterologous polypeptide and a signal peptide, said promoter being specifically active in mammary cells and said signal peptide being effective in directing the secretion of said polypeptide into the milk of said transgenic mammal;

(B) producing milk from said transgenic mammal, wherein said milk contains said polypeptide;

(C) collecting said milk; and (D) isolating said polypeptide from said milk.

20. The process of claim 19, wherein said transgenic non-human mammal is selected from the group consisting of mice, rats, rabbits, pigs, sheep, goats and cows.

21. The process of claim 20, wherein said transgenic non-human mammal is a sheep.

22. The process of claim 20, wherein said transgenic non-human mammal is a goat.

23. The process of claim 20, wherein said transgenic non-human mammal is a cow.

24. The mammal of claim 20, wherein said transgenic non-human mammal is a pig.

25. The process of claim 19, wherein said heterologous polypeptide is a blood protein.

26. The process of claim 25, wherein said blood protein is protein C, Factor IX, fibrinogen or Factor VIII.

27. The process of claim 19, wherein said heterologous polypeptide is protein C, wherein the activated form of said secreted protein C has an enzymatic activity of at least 50% as plasma-derived protein C, and wherein said transgenic mammal is selected from the group consisting of mice, rats, rabbits, pigs, sheep, goats and cows.

28. The process of claim 19, wherein said DNA sequence encoding the heterologous polypeptide comprises the human protein C gene from 21 basepairs upstream of the protein C start codon to the NheI site in the 3' end of the protein C gene.

29. The process of claim 19, wherein said DNA sequence encoding said heterologous polypeptide further comprises regulatory elements located in the non-coding regions of the heterologous protein gene, wherein said regulatory elements are at least one of the AUG start codon, donor and acceptor splice signals, the secretion peptide, translation termination signal, transcription termination signal, and polyadenylation signal.

* * * * *